(12) United States Patent
Barber et al.

(10) Patent No.: US 6,605,429 B1
(45) Date of Patent: Aug. 12, 2003

(54) GENE FUNCTIONAL ANALYSIS AND DISCOVERY USING RANDOMIZED OR TARGET-SPECIFIC RIBOZYME GENE VECTOR LIBRARIES

(75) Inventors: Jack R. Barber, San Diego, CA (US); Peter Welch, San Diego, CA (US); Soonpin Yei, Carlsbad, CA (US); Richard Tritz, San Diego, CA (US)

(73) Assignee: Immusol, Incorporated, San Diego, CA (US)

( * ) Notice: Subject to any disclaimer, the term of this patent is extended or adjusted under 35 U.S.C. 154(b) by 0 days.

(21) Appl. No.: 09/355,221

(22) PCT Filed: Jan. 21, 1998

(86) PCT No.: PCT/US98/01196
§ 371 (c)(1),
(2), (4) Date: Nov. 8, 1999

(87) PCT Pub. No.: WO98/32880
PCT Pub. Date: Jul. 30, 1998

Related U.S. Application Data

(60) Provisional application No. 60/037,352, filed on Jan. 23, 1997.

(51) Int. Cl.[7] .............................. C12Q 1/68; C12Q 1/02; C12P 19/34; C07H 21/04; C12N 15/09
(52) U.S. Cl. .......................... 435/6; 435/91.31; 435/29; 435/320.1; 536/24.5
(58) Field of Search ...................... 435/6, 91.31, 320.1, 435/29, 325; 514/44; 536/23.1, 23.2, 24.5

(56) References Cited

U.S. PATENT DOCUMENTS

| | | | |
|---|---|---|---|
| 5,254,678 A | 10/1993 | Haseloff et al. | 536/23.2 |
| 5,270,163 A | 12/1993 | Gold et al. | 435/6 |
| 5,354,855 A | 10/1994 | Cech et al. | 536/24.1 |
| 5,496,698 A | 3/1996 | Draper et al. | 435/6 |
| 5,567,588 A | 10/1996 | Gold et al. | 435/6 |
| 5,574,143 A | 11/1996 | Haselhoff et al. | 536/23.2 |
| 5,574,967 A | 11/1996 | Dent et al. | 455/12.1 |
| 5,580,967 A | 12/1996 | Joyce | 536/23.2 |
| 5,595,877 A | 1/1997 | Gold et al. | 435/6 |
| 5,610,054 A | 3/1997 | Draper | 435/363 |
| 5,616,459 A * | 4/1997 | Krammer et al. | 435/5 |
| 5,637,459 A | 6/1997 | Burke et al. | 435/6 |
| 5,670,637 A | 9/1997 | Gold et al. | 536/22.1 |
| 5,683,867 A | 11/1997 | Biesecker et al. | 435/6 |
| 5,688,935 A | 11/1997 | Stephens et al. | 536/23.1 |
| 5,696,249 A | 12/1997 | Gold et al. | 536/23.1 |
| 5,705,337 A | 1/1998 | Gold et al. | 435/6 |
| 5,712,375 A | 1/1998 | Jensen et al. | 530/412 |
| 5,723,289 A | 3/1998 | Eaton et al. | 435/6 |
| 5,723,592 A | 3/1998 | Eaton et al. | 536/23.1 |
| 5,750,342 A | 5/1998 | Stephens et al. | 435/6 |
| 5,759,773 A * | 6/1998 | Tyagi et al. | 435/6 |
| 5,763,177 A | 6/1998 | Gold et al. | 435/6 |
| 5,763,566 A | 6/1998 | Jensen et al. | 530/350 |
| 5,763,595 A | 6/1998 | Gold et al. | 536/22.1 |
| 5,773,598 A | 6/1998 | Burke et al. | 536/231 |
| 5,789,157 A | 8/1998 | Jensen et al. | 435/6 |
| 5,789,160 A | 8/1998 | Eaton et al. | 435/6 |
| 5,817,785 A | 10/1998 | Gold et al. | 536/23.1 |
| 5,843,653 A | 12/1998 | Gold et al. | 435/6 |
| 5,853,984 A | 12/1998 | Davis et al. | 435/6 |
| 5,858,660 A | 1/1999 | Eaton et al. | 435/6 |
| 5,861,254 A | 1/1999 | Schneider et al. | 435/6 |
| 5,864,026 A | 1/1999 | Jensen et al. | 536/23.1 |
| 5,874,218 A | 2/1999 | Drolet et al. | 435/6 |
| 6,107,028 A * | 8/2000 | Kay et al. | 435/6 |

FOREIGN PATENT DOCUMENTS

| | | |
|---|---|---|
| WO | WO 92/01806 | 2/1992 |
| WO | WO 93/23569 | 11/1993 |
| WO | WO 94/26877 | 11/1994 |
| WO | WO 96/01314 | 1/1996 |

OTHER PUBLICATIONS

Welch et al. Apotential Therapeutic application of hairpin robizymes: In vitro and in vivo studies of gene therapy for hepatitis C virus infection. Gene therapy. vol. 3, lines 994–1001, Dec. 1996.*
Lieber et al. Selection of Efficient Cleavage sites in target RNAs by using a ribozyme expression library. Molecular and Cellular Biology. vol. 15, No. 1, pp. 540–551, Jan. 1995.*
Cameron et al. Specific gene suppression by engineered ribozymes in monkey cells. Proc. Natl. Acad. Sci. USA vol. 86, pp. 9139–9143, Dec. 1989.*
Rosenberg et al. Gene Therapist, Heal Thyself. Science vol. 287, No. 5459, p. 1751, Mar. 2000.*
Ojwang et al. Inhibition of human immunodeficiency virus type 1 expression by a hairpin ribozyme. Proc. Natl. Acad. Sci. USA vol. 89, pp. 10802–10806, Nov. 1992.*
Akhtar et al., "Molecular DIY with hairpins and hammerheads," *Nature Medicine* 1:300–302 (1995).
Anderson et al., "Mutagenesis of the hairpin ribozyme," *Nucleic Acids Res.* 22:1096–1100 (1994).
Bassi et al., "The ion–induced folding of the hammerhead ribozyme: Core sequence changes that perturb folding into the active conformation," *RNA* 2:756 768 (1996).
Bennett and Cullimore, "Selective cleavage of closely–related mRNAs by synthetic ribozymes," *Nucleic Acids Research* 20:831–837 (1992).

(List continued on next page.)

*Primary Examiner*—Kenneth R. Horlick
*Assistant Examiner*—Cynthia Wilder
(74) *Attorney, Agent, or Firm*—Townsend and Townsend and Crew LLP

(57) ABSTRACT

The present invention provides a hairpin ribozyme library having a randomized recognition sequence, packaged in a vector and operably linked to a promoter suitable for high level expression in a wide variety of cells. The invention comprises using the library in a variety of selection protocols for identifying, isolating and characterizing known or unknown target RNAs, to reveal the phenotypic effects of such cleavage, and to identify the gene products that produce those phenotypic effects.

6 Claims, 10 Drawing Sheets

OTHER PUBLICATIONS

Figure 1:
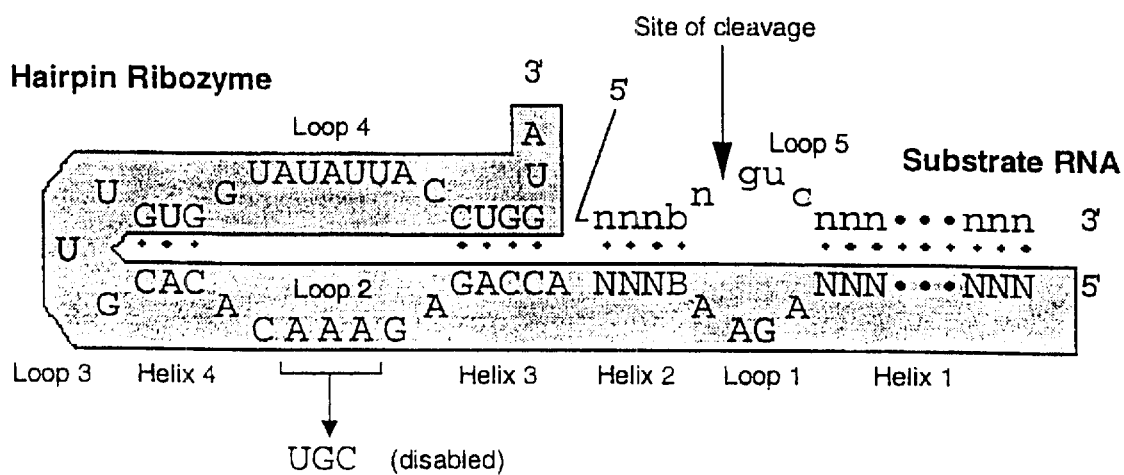

Berzal–Herranz et al., "In vitro selection of active hairpin ribozymes by sequential RNA–catalyzed cleavage and ligation reactions," *Genes and Development* 6:129–134 (1992).

Bratty et al., "The hammerhead RNA domain, a model ribozyme" *Biochim. et Biophys. Acta* 1216:345–359 (1993).

Cameron and Jennings, "Specific gene suppression by engineered ribozymes in monkey cells," *Proc. Natl. Acad. Sci. USA* 86:9139–9143 (1989).

Campbell and Cech, "Identification of ribozymes within a ribozyme library that efficiently cleave a long substrate RNA," *RNA* 1:598–609 (1995).

Cech and Bass, "Biological catalysis by RNA," *Ann. Rev. Biochem* 55:599–629 (1986).

Cech and Uhlenbeck, "Hammerhead nailed down," *Nature* 372:39–40 (1994).

Chowrira et al., "Ionic requirements for RNA binding, cleavage, and ligation by the hairpin ribozyme," *Biochemistry* 32:1088–1095 (1993).

De Young et al., "Catalytic properties of hairpin ribozymes derived from chicory yellow mottle virus and arabis mosaic virus satellite RNAs," *Biochemistry* 34:15785–15791 (1995).

Dropulić et al., "Functional characterization of a U5 ribozyme: intracellular suppression of human immunodeficiency virus type 1 expression," *J. Virol.* 66:1432–1441 (1992).

Feldstein et al., "Two sequences participating in the autolytic processing of satellite tobacco ringspot virus complementary RNA," *Gene* 82:53–61 (1989).

Gold et al., "Diversity of oligonucleotide functions," *Annu. Rev. Biochem.*, 64:763–797 (1995).

Gold et al., "From oligonucleotide shapes to genomic SELEX: Novel biological regulatory loops," *Proc. Natl. Acad. Sci. USA*, 94:59–64 (1997).

Gold et al., "SELEX and the evolution of genomes," *Current Opinion in Genetics & Development*, 7:848–851 (1997).

Hampel et al., "Hairpin catalytic RNA model: evidence for helices and sequence requirement for substrate RNA," *Nucl. Acids Res.* 18:299–304 (1990).

Kijima et al., "Therapeutic applications of ribozymes," *Pharmac. Ther.* 68:247–267 (1995).

Leavitt et al., "Transfer of an anti–HIV–1 ribozyme gene into primary human lymphocytes," *Human Gene Therapy* 5:1115–1120 (1994).

Lieber and Strauss, "Selection of efficient cleavage sites in target RNAs by using a ribozyme expression library," *Mol. Cell. Biol.* 15:540–551 (1995).

Macejak and Draper, "Design of quasi–random ribozyme expression vectors," *J. Cell. Biochem.* Supplement 17E, S206:202 (1993).

Ojwang et al., "Inhibition of human immunodeficiency virus type 1 expression by a hairpin ribozyme ," *Proc. Natl. Acad. Sci. USA* 89:10802–10806 (1992).

Sioud et al., "Preformed ribozyme destroys tumour necrosis factor mRNA in human cells," *J. Mol. Biol.* 223:831–835 (1992).

Thompson et al., "Ribozymes in gene therapy," *Nature Medicine* 1:277–278 (1995).

Welch et al., "A potential therapeutic application of hairpin ribozymes: in vitro and in vivo studies of gene therapy for hepatitis C virus infection," *Gene Therapy* 3:994–1001 (1996).

Yamada et al., "Intracellular immunization of human T cells with a hairpin ribozyme against human immunodeficiency vrus type 1," *Gene Therapy* 1:38–45 (1994).

Yamada et al., "Activity and cleavage site specificity of anti–HIV–1 ribozyme in human T cells," *Virology* 205:121–126 (1994).

Yu et al., "A hairpin ribozyme inhibits expression of diverse strains of human immunodeficiency virus type 1," *Proc. Natl. Acad. Sci. USA* 90:6340–6344 (1993).

Yu et al., "Intracellular immunization of human fetal cord blood stem/progenitor cells with a ribozyme against human immunodeficiency virus type 1," *Proc. Natl. Acad. Sci. USA* 92:699–703 (1995).

Yu et al., "In Vitro and in Vivo characterization of a second functional hairpin ribozyme against HIV–1," *Virology* 206:381–386 (1995).

* cited by examiner

FIGURE 1  The Hairpin Ribozyme

Figure 4:
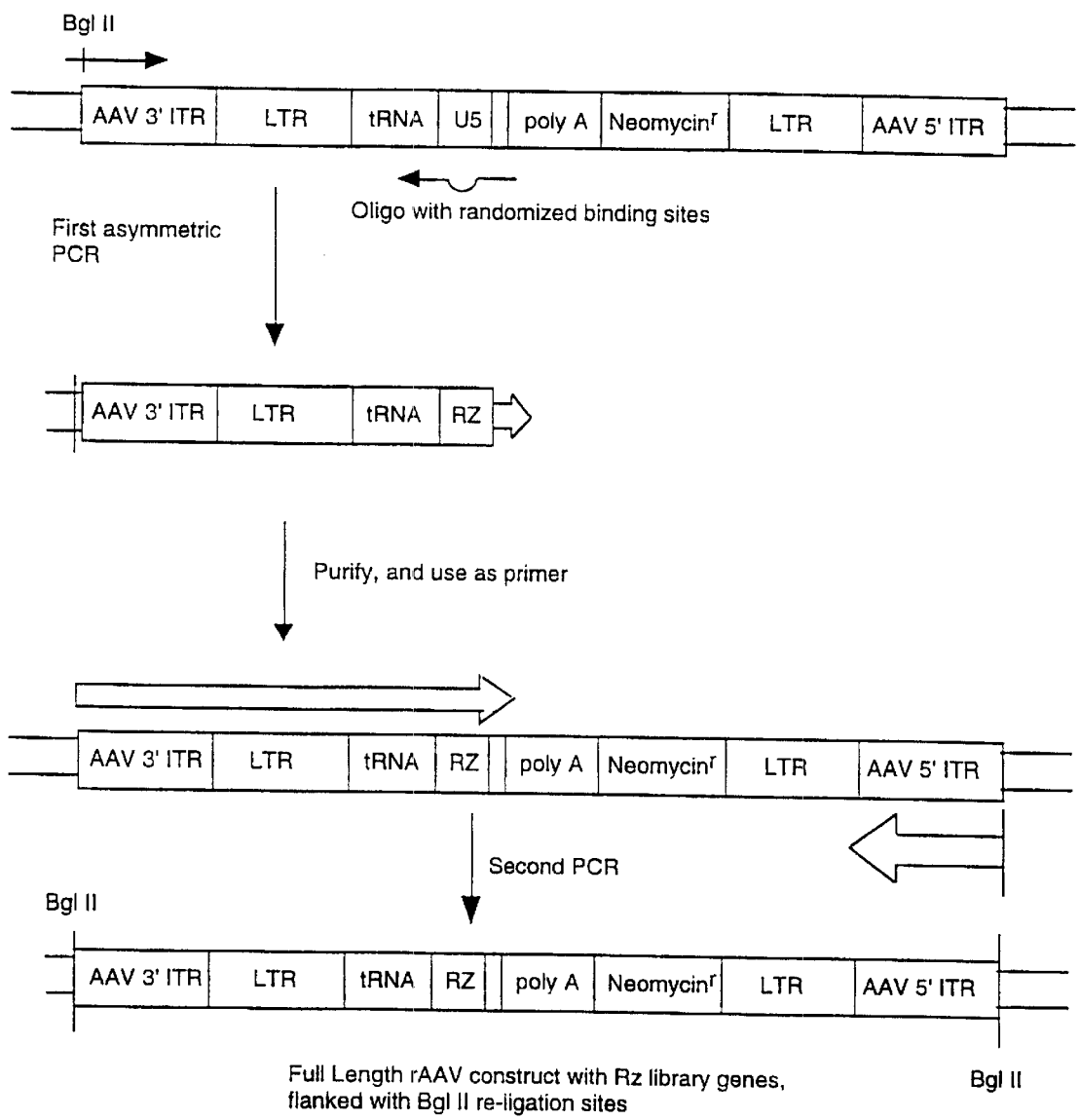

FIGURE 4    Generation of rAAV-RZ-lib provector by PCR

FIGURE 5  PRODUCTION SCHEME FOR ADENO-ASSOCIATED VIRAL VECTOR

FIGURE 7     Attaching RNA target to solid support
Binding target RNA at 5' end:
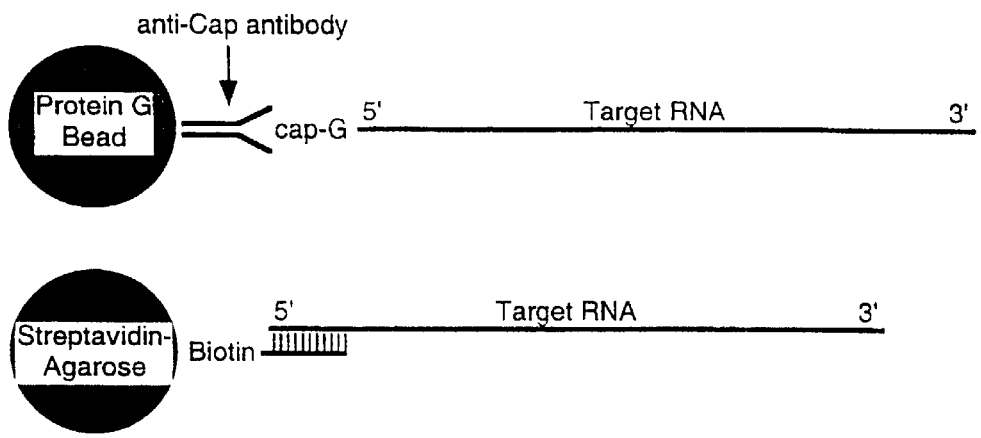
Binding target RNA at 3' end:
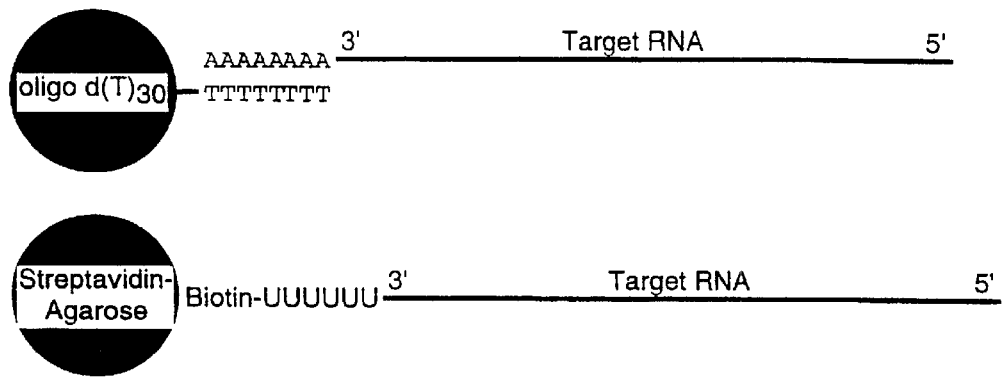

FIGURE 8    In vitro selection of optimal ribozymes
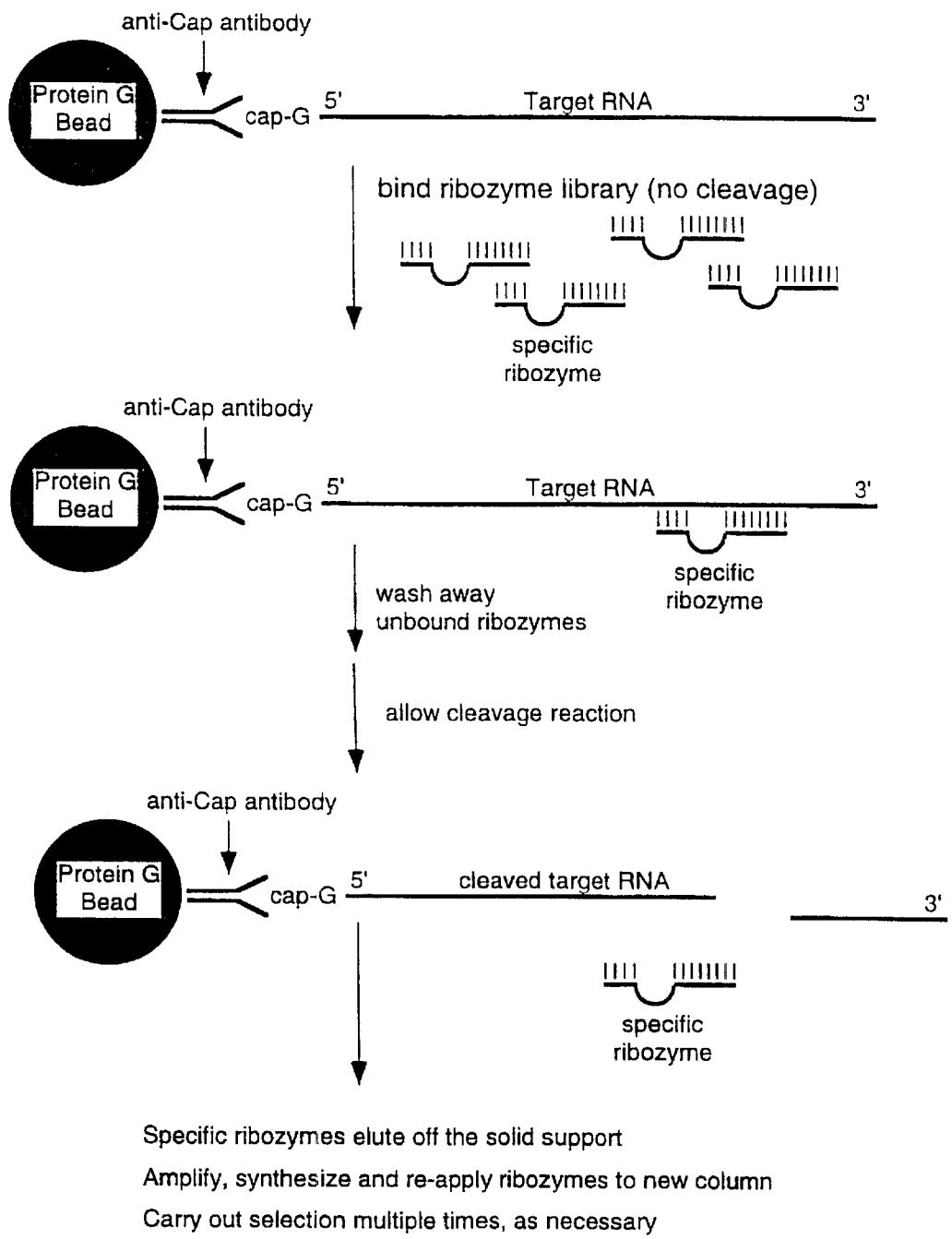

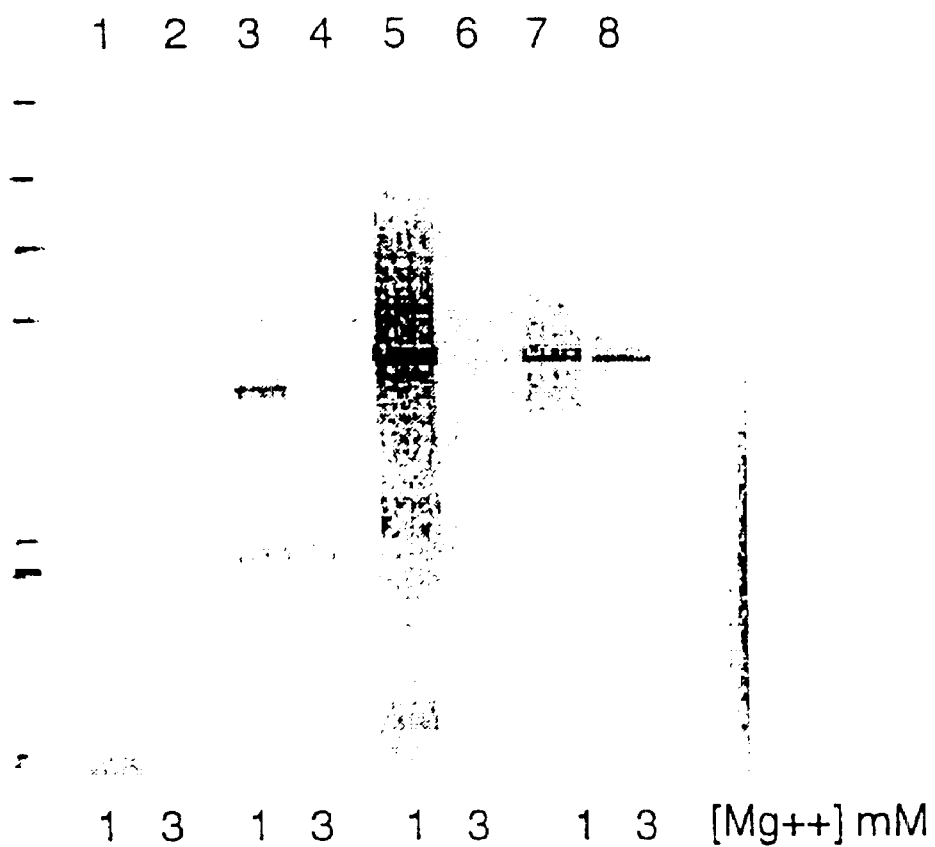
FIGURE 9  AAV stable integration

FIGURE 10  Trans Cleavage and Ligation
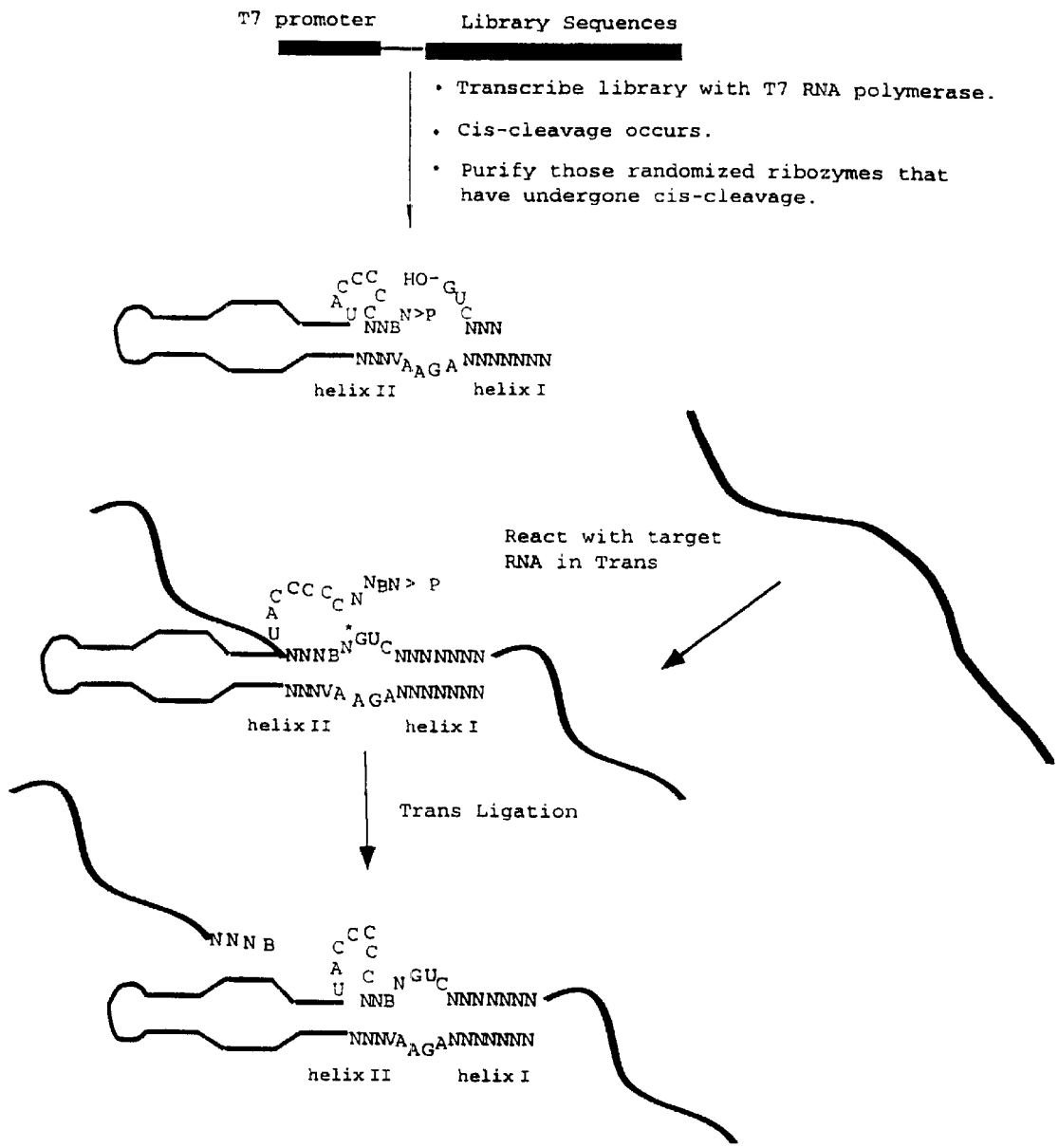
- Trans-ligated products are isolated and amplified by RT-PCR.
- Trans-ligated ribozymes can then be further amplified and subcloned into AAV vectors for production of a target specific ribozyme gene vector library.

SEQUENCE LISTING

<160> NUMBER OF SEQ ID NOS: 14

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:5' primer

<400> SEQUENCE: 1
gggtaatacg actcactata gggatcctcg atgaagc                          37

<210> SEQ ID NO 2
<211> LENGTH: 76
<212> TYPE: DNA

<213> ORGANISM: Artificial Sequence
<220> FEATURE:
<223> OTHER INFORMATION: Description of Artificial Sequence:3' Synth
      primer
<220> FEATURE:
<221> NAME/KEY: misc_feature
<222> LOCATION: (1)..(76)
<223> OTHER INFORMATION: n = g, a, c or t

<400> SEQUENCE: 2
tcgacgcgta ccaggtaata taccacaacg tgtgtttctc tggtnnnntt ctnnnnnnng    60
cttcatcgag gatccc                                                   76

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:3' primer

<400> SEQUENCE: 3
tcgacgcgta ccaggtaata taccacaacg tgtgtttctc tggt                    44

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence:3' disabeled
      primer

<400> SEQUENCE: 4
tcgacgcgta ccaggtaata taccacaacg tgtgacgctc tggt                    44

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence:3'-AAV-ITR
      primer

<400> SEQUENCE: 5
aggaagatct ctggcgcgct cgctcgctca ctgaggccgc ccgg                    44

<210> SEQ ID NO 6
<211> LENGTH: 81
<212> TYPE: DNA
<213> ORGANISM: Artificial Sequence
<220> FEATURE:
<223> OTHER INFORMATION: Description of Artificial Sequence:
      tRNA-ribozyme lib PCR primer (tRNA-Rz lib primer)
<220> FEATURE:
<221> NAME/KEY: misc_feature
<222> LOCATION: (1)..(81)
<223> OTHER INFORMATION: n = g, a, c or t

<400> SEQUENCE: 6
taccaggtaa tataccacaa cgtgtgtttc tctggtnnnb ttctnnnnnn ntggatcctg    60
tttccgcccg gtttcgaacc g                                             81

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence:5'-AAV-ITR -continued primer

<400> SEQUENCE: 7
aggaagatct cagcagctgc gcgctcgctc gctcactgag g          41

<210> SEQ ID NO 8
<211> LENGTH: 47
<212> TYPE: RNA
<213> ORGANISM: Artificial Sequence
<220> FEATURE:
<223> OTHER INFORMATION: Description of Artificial Sequence:hairpin
      ribozyme
<220> FEATURE:
<221> NAME/KEY: misc_feature
<222> LOCATION: (1)..(11)
<223> OTHER INFORMATION: n = g, a, c or u

<400> SEQUENCE: 8
nnnagaabnn naccagagaa acacacguug ugguauauua ccuggua          47

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence:self-cleaved
      auto-catalytic ribozyme sequence
<220> FEATURE:
<221> NAME/KEY: misc_feature
<222> LOCATION: (1)..(11)
<223> OTHER INFORMATION: n = g, a, c or u

<400> SEQUENCE: 9 uaccccnnb n          11

<210> SEQ ID NO 10
<211> LENGTH: 15
<212> TYPE: RNA
<213> ORGANISM: Artificial Sequence
<220> FEATURE:
<223> OTHER INFORMATION: Description of Artificial Sequence:self-cleaved
      auto-catalytic ribozyme sequence
<220> FEATURE:
<221> NAME/KEY: misc_feature
<222> LOCATION: (1)..(15)
<223> OTHER INFORMATION: n = g, a, c or u

<400> SEQUENCE: 10
nnnnnnnaga avnnn          15

<210> SEQ ID NO 11
<211> LENGTH: 15
<212> TYPE: RNA
<213> ORGANISM: Artificial Sequence
<220> FEATURE:
<223> OTHER INFORMATION: Description of Artificial Sequence:portion of
      charged ribozyme ligated to cleavage product
<220> FEATURE:
<221> NAME/KEY: misc_feature
<222> LOCATION: (1)..(15)
<223> OTHER INFORMATION: n = g, a, c or u

<400> SEQUENCE: 11
nnnbngucnn nnnnn          15

<210> SEQ ID NO 12
<211> LENGTH: 21
<212> TYPE: RNA
<213> ORGANISM: Artificial Sequence

```
<220> FEATURE:
<223> OTHER INFORMATION: Description of Artificial Sequence:
      trans-ligated ribozyme, target specific ribozyme
<220> FEATURE:
<221> NAME/KEY: misc_feature
<222> LOCATION: (1)..(21)
<223> OTHER INFORMATION: n = g, a, c or u

<400> SEQUENCE: 12 uaccccennb ngucnnnnnn n                                              21

<210> SEQ ID NO 13
<211> LENGTH: 11
<212> TYPE: RNA
<213> ORGANISM: Artificial Sequence
<220> FEATURE:
<223> OTHER INFORMATION: Description of Artificial Sequence:substrate
      RNA
<220> FEATURE:
<221> NAME/KEY: misc_feature
<222> LOCATION: (1)..(11)
<223> OTHER INFORMATION: n = g, a, c or u

<400> SEQUENCE: 13
nnnbngucnn n                                                         11

<210> SEQ ID NO 14
<211> LENGTH: 16
<212> TYPE: RNA
<213> ORGANISM: Artificial Sequence
<220> FEATURE:
<223> OTHER INFORMATION: Description of Artificial Sequence:GUC ribozyme
      target cleavage site
<220> FEATURE:
<221> NAME/KEY: misc_feature
<222> LOCATION: (1)..(16)
<223> OTHER INFORMATION: n = g, a, c or u

<400> SEQUENCE: 14
nnnbngucnn nnnnnn                                                    16
```

GENE FUNCTIONAL ANALYSIS AND DISCOVERY USING RANDOMIZED OR TARGET-SPECIFIC RIBOZYME GENE VECTOR LIBRARIES

This application claims the benefit of Provisional applications No. 60/037352, filed Jan. 23, 1997.

A. BACKGROUND OF THE INVENTION

1. Field of the Invention

This invention relates generally to methods for using hairpin ribozymes to inactivate target RNA molecules. The present invention specifically provides methods for identifying, isolating, and characterizing unknown genes and gene products responsible for detectable phenotypic traits or for characterizing unknown phenotypic effects of known genes, and methods of inactivating target RNAs. Compared to other known ribozymes, the hairpin ribozyme has been discovered to be uniquely effective as a randomized antisense tool.

2. Related Art

A ribozyme is an RNA molecule that catalytically cleaves other RNA molecules. Different kinds of ribozymes have been described, including group I ribozymes, hammerhead ribozymes, hairpin ribozymes, RNAse P, and axhead ribozymes. See Castanotto et al. (1994)*Advances in Pharmacology* 25:289–317 for a general review of the properties of different ribozymes.

The general features of hairpin ribozymes are described e.g., in Hampel et al. (1990) *Nucl. Acids Res.* 18:299–304; Hampel et al. (1990) European Patent Publication No. 0 360 257; U.S. Pat. No. 5,254,678, issued Oct. 19, 1993; Wong-Staal et al., WO 94/26877; Ojwang et al. (1993) *Proc. Natl. Acad. Sci. USA* 90:6340–6344; Yamada et al. (1994) *Human Gene Therapy* 1:39–45; Leavitt et al. (1995) *Proc. Natl. Acad. Sci. USA* 92:699–703; Leavitt et al. (1994) *Human Gene Therapy* 5:1151–1120; and Yamada et al. (1994) *Virology* 205:121–126; see FIG. 1. Hairpin ribozymes typically cleave one of two target sequences, NNNNN*GUCNNNNNNNN or NNNNN*GUANNNNNNNN (* denotes the cleavage site, and N can be any nucleotide). See, De Young et al. (1995) *Biochemistry* 34:15785–15791. The products of the cleavage reaction are a 5' fragment terminating in a 2',3' cyclic phosphate and a 3' fragment bearing a newly formed 5'-OH. The reaction is reversible; ribozymes also catalyze the formation of phosphodiester bonds. See generally, Buzayan et al. (1986) *Nature* 323:349–352; Gerlach et al. (1986) *Virology* 151:172–185; Hampel et al. (1989) *Biochemistry* 28:4929–4933; Gerlach et al. (1989) *Gene* 82:43–52; Feldstein et al. (1989) *Gene* 82:53–61; and Hampel et al. Australian Patent No. AU-B-41594/89.

Ribozymes can be used to engineer RNA molecules prior to reverse transcription and cloning, in a manner similar to the DNA endonuclease "restriction" enzymes. The production of specific ribozymes which target particular sequences is taught in the art (see, e.g., Yu et al. (1993) *Proc. Natl. Acad. Sci. USA* 90:6340–6344 and Dropulic et al. (1992) *J. Virol.* 66(3):1432–1441; Wong-Staal et al., WO 94/26877). Ribozymes which cleave or ligate a particular RNA target sequence can be expressed in cells to prevent or promote expression and translation of RNA molecules comprising the target sequence. For instance, expression of hairpin ribozymes which specifically cleave human immunodeficiency (HIV) RNAs prevent replication of the virus in cells. See, Yu et al. (1993) *Proc. Natl. Acad. Sci. USA* 90:6340–6344; Yamada et al. (1994) *Virology* 205:121–126; Yamada et al. (1994) *Gene Therapy* 1:38–45; Yu et al. (1995) *Virology* 206:381–386; Yu et al. (1995) *Proc. Nat. Acad. Sci.* 92:699–703; and Wong-Staal et al. WO 94/26877 (PCT/US94/05700). The trans-splicing activity of ribozymes can be used to repair defective mRNA transcripts within cells and restore gene expression. Sullenger and Cech (1994) *Nature* 371:619–622. Quasi-random ribozyme expression vectors were reportedly used to clone target specific ribozymes. Macjak and Draper (1993) *J. Cell. Biochem.* Supplement 17E, S206:202. A hammerhead ribozyme library comprising a randomized recognition sequence was used for in vitro selection of ribozymes which actively cleave a specific target RNA (Lieber and Strauss (1995) *Mol. Cell. Biol.* 15:540–551; patent publication 96/01314); ribozymes selected by this method were then expressed in tissue culture cells (id.) and in transgenic mice (Lieber and Kay (1996) *J. Virol.* 70:3153–3158). In addition, hammerhead ribozyme libraries comprising a randomized catalytic region have been used to select ribozymes that efficiently cleave a specific target RNA. Patent publication WO 92/01806. A library of the ribozyme form of the group I intron of *Tetrahymena thermophila* having a partially randomized recognition sequence was used for in vitro selection of ribozymes which actively cleave a specific target RNA. Campbell and Cech (1995) *RNA* 1:598–609.

However, even when both the sequence of the cleavage sites of a specific target RNA and the recognition sequences of ribozymes that cleave that specific RNA are known, targeted cleavage of RNA in vivo has been difficult to achieve (See, e.g., Ojwang et al. (1992) *Proc. Natl. Acad. Sci. USA* 89:10802–10806), in part for the following reasons: (a) The target site may be hidden within the folds of secondary structure in the substrate RNA, or by interaction with RNA binding molecules. (b) The substrate RNA and the ribozyme may not be present in the same cellular compartment. (c) The ribozyme may be inhibited or inactivated in vivo, either because it is degraded, or because it assumes a secondary structure in vivo that is incompatible with catalytic activity, or because of interactions with cellular molecules. The observed biological effects in some instances can be attributed to simple binding of the ribozyme, as opposed to binding and cleavage. (d) The ribozyme is not produced in sufficient quantities.

The present invention addresses these and other problems.

B. SUMMARY OF THE INVENTION

In the present invention, a hairpin ribozyme gene library having a randomized target recognition sequence, packaged in a vector which is suitable for high level transduction and expression in a wide variety of cells, is used to identify, isolate, and characterize unknown genes and gene products responsible for detectable phenotypic traits, and to characterize unknown phenotypic effects of known genes. In a preferred embodiment, the vector is an adeno-associated virus vector (AAV). The ribozyme gene is preferably operably linked to a transcriptional promoter that allows for optimal inhibition of target RNA expression in vivo, such as a pol III promoter. The result is an unexpectedly high level of expression of the ribozyme gene products. This efficient expression in turn makes possible the in vivo or in vitro selection of ribozyme genes that are active in vivo, even when the target site is not known.

In one embodiment, the invention comprises a method of correlating expression of a nucleic acid that encodes a hairpin ribozyme with the appearance or loss of a detectable phenotype which results from the inhibition or expression of a cellular gene not previously known to result in said phenotype, which involves generating transduced cell clones which express at least one reporter gene or otherwise selectable marker and one or more ribozyme genes from a library of hairpin ribozyme-encoding nucleic acids having randomized target recognition sequences, detecting a phenotypic difference between a transduced cell that expresses said hairpin ribozyme, and a cell of the parental cell line that does not express said hairpin ribozyme, deconvoluting if necessary, isolating and sequencing the ribozyme present in transduced cells that express a selected phenotype. The hairpin ribozyme-encoding nucleic acid is operably linked to an inducible or constitutive promoter. In this and other embodiments, the cells can be eukaryotic, particularly mammalian cells, and the cellular gene can be from the genome of the transformed cell.

In another embodiment, the invention comprises a method of determining unknown phenotypic effects of a coding nucleic acid of known sequence, comprising: simultaneously expressing within a same cell a coding nucleic acid of known sequence and also a hairpin ribozyme that recognizes at least one GUC site present in said coding nucleic acid of known sequence; and then detecting phenotypic differences between cells that simultaneously express said coding nucleic acid of known sequence and also a hairpin ribozyme that recognizes said at least one GUC site present in said coding nucleic acid of known sequence, and cells that express only said coding nucleic acid of known sequence, or cells that express only said hairpin ribozyme that recognizes a GUC site present in said coding nucleic acid of known sequence.

In another embodiment, the invention comprises a method of identifying a nucleic acid whose gene product mediates binding to a selected ligand, comprising transducing a population of parental cells which express a nucleic acid whose gene product mediates binding to a selected ligand with vectors that comprise a library of hairpin ribozyme-encoding nucleic acids having randomized recognition sequences and with a nucleic acid that encodes at least one reporter gene; identifying and cloning a transduced cell that does not bind to said selected ligand, to yield a population of cloned cells that do not bind to said selected ligand; isolating the ribozyme that is expressed in said cloned transduced cells; and determining the sequence of the recognition sequence of the ribozyme; making an oligonucleotide probe consisting of the recognition sequence of the ribozyme; and identifying a nucleic acid whose gene product is recognized by the ribozyme using the oligonucleotide probe. The selected ligand may be one that binds to a cell surface receptor. The ligand may be present on a viral particle, a growth factor, a differentiation factor, any protein with an antibody directed against it. It can be identified by FACS or affinity separation techniques. The ligand may belong to the group consisting of hormone receptors, receptors for molecules that induce apoptosis, and drug receptors.

In another embodiment, the invention comprises a method of identifying regulatory gene products and genes that control the expression of a particular selected nucleic acid, by genetically engineering a population of cells to express in every cell a selected gene operably linked to one or more reporter genes in a vector and at least one member of a library of hairpin ribozyme-encoding nucleic acids having randomized recognition sequences; isolating and cloning a genetically engineered cell wherein the level of expression of the reporter gene is measurably different from that of cells that express the reporter gene but do not express a member of said library of hairpin ribozyme-encoding nucleic acids; and identifying a nucleic acid whose gene product is recognized by a ribozyme expressed in the cloned genetically engineered cells.

In yet another embodiment, the invention comprises a method of identifying a gene whose gene product confers sensitivity to a selected chemical compound or sensitivity to a cytolytic virus or any other microbial entity, comprising transducing a population of parental cells which are sensitive to a selected chemical compound or virus or microbe with vectors that comprise a library of hairpin ribozyme-encoding nucleic acids having randomized recognition sequences; identifying and cloning a transduced cell that is resistant to said selected chemical compound or virus or microbe, to yield a population of cloned transduced cells that are resistant to said selected chemical compound or virus or microbe; and identifying a nucleic acid whose gene product is recognized by a ribozyme expressed by the cloned transduced cells of step b.

In yet another embodiment, the invention comprises a method of identifying a gene whose gene product confers sensitivity to a non-cytolytic virus, comprising transducing a population of parental cells which are sensitive to a selected virus with vectors that comprise a library of hairpin ribozyme-encoding nucleic acids having randomized recognition sequences; identifying and cloning a transduced cell that is resistant to said virus. Resistant cells can be identified by sorting for those cells that lack expression of a viral antigen (ideally a cell surface associated antigen) following infection. Alternatively, cells expressing ribozymes can be selected based on their ability to inactivate expression of one or more viral promoters through the inactivation of viral or cellular genes necessary for transactivation or transexpression of the viral promoter, by linking a selectable marker to the viral promoter and selecting for the loss of reporter gene function.

In yet another embodiment, the invention comprises the generation of a target nucleic acid and an in vitro method of detecting a ribozyme that cleaves said target, comprising hybridizing a library of hairpin ribozyme-encoding nucleic acids having randomized recognition sequences in vitro to a target nucleic acid (RNA or DNA that has been converted to RNA) under stringent hybridization conditions in a solution that does not permit cleavage, wherein the ribozymes having recognition sequences that are complementary to the target nucleic acid hybridize to the recognition site on the target nucleic acid but do not cleave the target nucleic acid; and collecting one or more ribozymes that bind to the target nucleic acid. The target nucleic acid is preferably attached to a solid substrate and consists of RNA or DNA that has been converted to RNA, and can be derived from an isolated chromosome, an isolated nucleic acid that encodes a desired gene product, a selected isolated nucleic acid fragment; an isolated polycistronic nucleic acid; a cDNA library, and a total messenger RNA fraction of a cell. Furthermore, ribozymes with activity against said target can be amplified and the selection procedure can be repeated multiple times. Alternatively, the target nucleic acid is not attached to a solid support and the trans-ligation properties of the hairpin ribozyme are employed to "tag" the cleavage products. This ribozyme "tag" is then used to amplify the specific active ribozymes.

In a further embodiment, the invention comprises a method for identifying differentially-expressed genes between two cell types, using in vitro selection techniques that are technically easier than currently available methods. Further, the invention comprises identifying a ribozyme or ribozymes that will inactivate the differentially-expressed gene(s).

In another embodiment, the invention comprises an in vivo method of selecting at least one hairpin ribozyme gene that cleaves a target recognition site in a target nucleic acid, comprising generating cells that co-express a library of hairpin ribozyme-encoding nucleic acids having randomized recognition sequences and a nucleic acid that encodes at least one FACS-sortable or otherwise selectable reporter gene, wherein the gene product of at least one ribozyme-encoding nucleic acid cleaves a target sequence in a selected target nucleic acid; isolating and packaging the ribozyme-encoding nucleic acids of said cloned cells; then generating and cloning transduced cells that express at least one ribozyme-encoding nucleic acid whose gene product cleaves a target sequence; and isolating the ribozyme-encoding nucleic acid from the cloned cells.

In another embodiment, the invention comprises a method for identifying genes involved in cancer formation, such as oncogenes or tumor suppressors. This comprises transducing parental cells with vectors that comprise a library of hairpin ribozyme-encoding nucleic acids having randomized recognition sequences; identifying and cloning a transduced cell that has either: a) in the case of oncogenes, lost its transforming potential in tissue culture and nude mice or b) gained transformation capabilities in tissue culture and nude mice, as would be the case for loss of tumor suppressor function.

In another embodiment, the invention comprises a method of detecting a ribozyme that produces a detectable phenotype in a mammal, comprising generating transgenic or chimeric non-human mammals that express nucleic acids that encode hairpin ribozymes that recognize a selected target nucleic acid; screening transgenic mammals for a selected phenotype; and isolating and characterizing the ribozyme-encoding nucleic acids from the cells of the transgenic or chimeric animal. Preferably, the phenotype is a neurological disorder, such as Alzheimer's disease (Games et al. (1995) *Nature* 373:523; Moran et al. (1995) *PNAS USA* 92:5341).

In a separate embodiment, the invention comprises a target-specific ribozyme gene library, generated by collecting ribozymes that bind to and cleave a specific target sequence.

In another embodiment, the invention comprises a differential cell ribozyme gene library, composed of ribozymes that bind to a first cell line but not to a second cell line.

In yet another embodiment, the invention comprises a kit which includes a hairpin ribozyme library having a randomized recognition sequence, packaged in a vector which is suitable for high level expression in a wide variety of cells. The preferred vector is an adenoviral associated vector, and the ribozyme gene is preferably operably linked to a pol III promoter. The kit further comprises reagents and detailed instruction for use in the above methods of the invention.

C. BRIEF DESCRIPTION OF FIGURES AND TABLES

FIG. 1: The Hairpin Ribozyme

The hairpin ribozyme consists of a 50 to 54 nucleotide RNA molecule (SEQ ID NO:8; shaded, in uppercase letters) which binds and cleaves an RNA substrate (SEQ ID NO:13 lowercase letters). The catalytic RNA folds into a 2-dimensional structure that resembles a hairpin, consisting of two helical domains (Helix 3 and 4) and 3 loops (Loop 2, 3 and 4). Two additional helixes, Helix 1 and 2, form between the ribozyme and its substrate. Recognition of the substrate by the ribozyme is via Watson-Crick base pairing (where N or n=any nucleotide, b=C, G or U and B=the nucleotide complementary to b). The length of Helix 2 is fixed at 4 basepairs and the length of Helix 1 typically varies from 6 to 10 basepairs. The substrate must contain a GUC in Loop 5 for maximal activity, and cleavage occurs immediately 5' of the G as indicated by an arrow. The catalytic, but not substrate binding, activity of the ribozyme can be disabled by mutating the AAA in Loop 2 to CGU.

Figure 2:
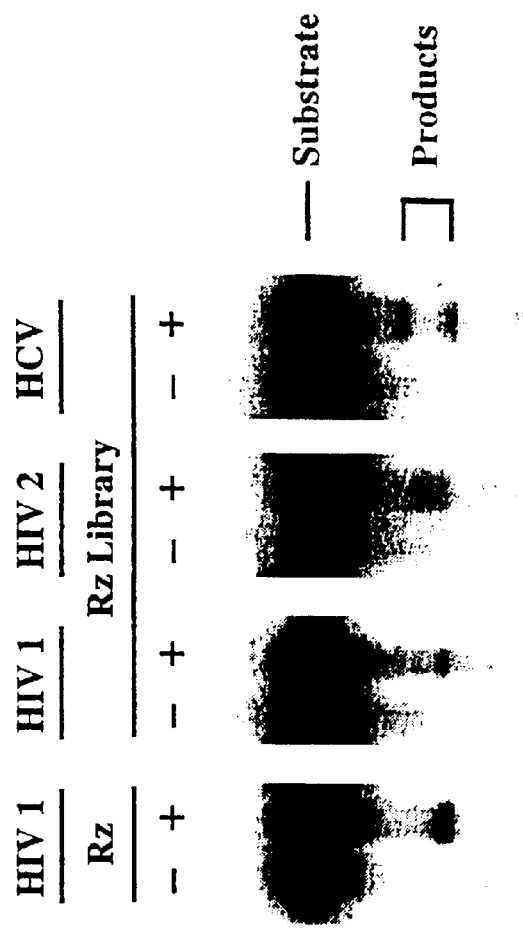

FIG. 2: Cleavage of Target Substrates by Hairpin Ribozyme Library

Detection of ribozyme activity of the library in vitro. Various known RNA substrates (HIV 1=pol 3308; HIV 2=env 7931; HCV=core 506) were cleaved with ribozymes transcribed from the library. When known, purified ribozyme was added at the concentration expected to be found in the library, the cleavage pattern between the purified ribozyme and the ribozyme library is identical when the same RNA substrate is used (HIV 1, ribozyme vs. ribozyme library).

Figure 3:
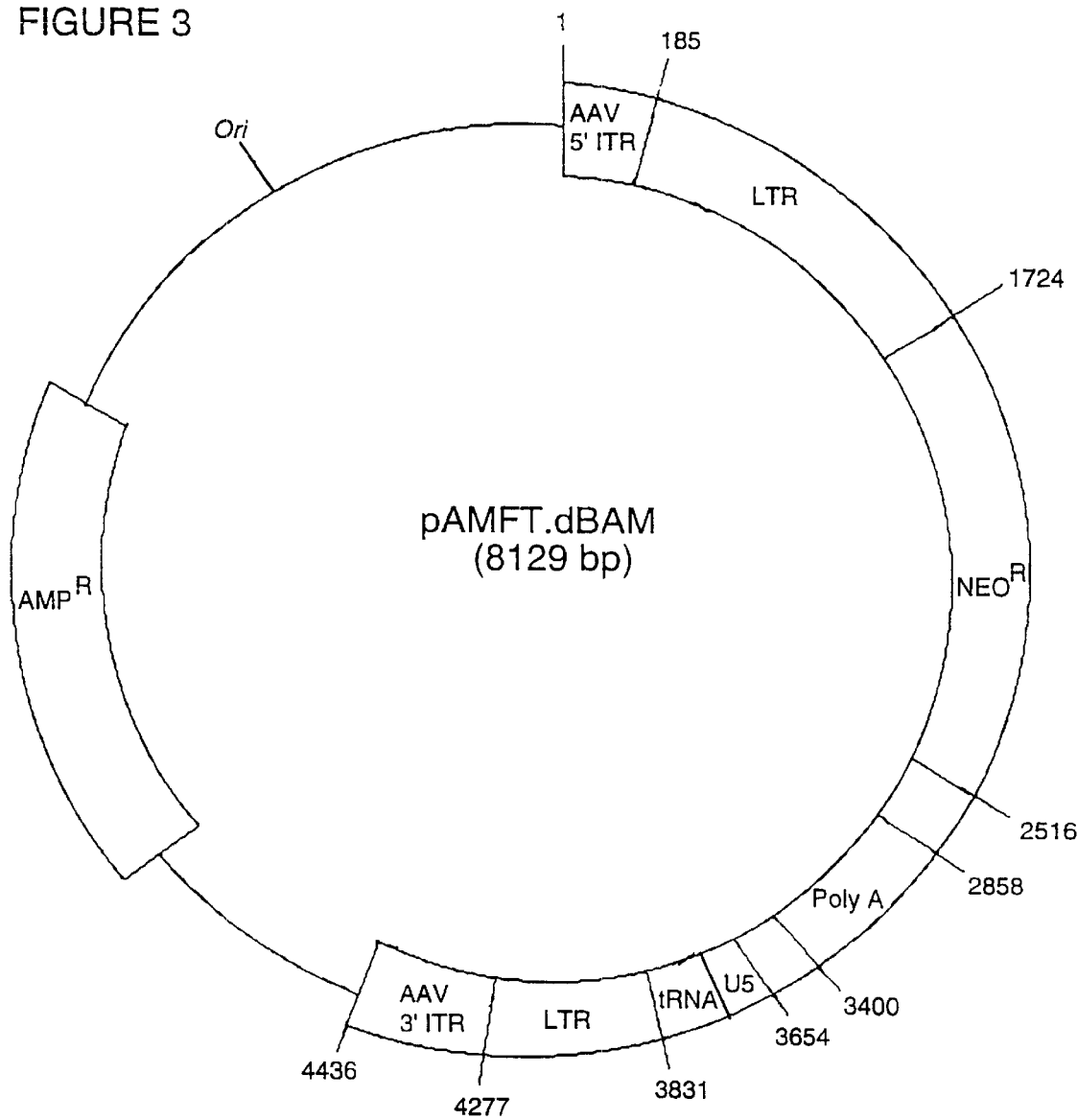

FIG. 3: AAV Plasmid (pAMFT-dBam)

Genomic organization of pAMFT.dBam, a recombinant plasmid from which infectious adeno-associated viral vector (rAAV) harboring an expression cassette for a hairpin ribozyme can be produced. The major components of this plasmid are: AAV 5'-ITR (inverted terminal repeat), neomycin resistance gene, hairpin ribozyme gene (denoted U5 in figure) under control of tRNA$^{val}$ pol III promoter, AAV 3'-ITR.

FIG. 4: Generation of rAAV-ribozyme Library Pro-vector by PCR

A schematic illustration showing how full length rAAV constructs containing the ribozyme library genes can be generated by two rounds of PCR. The resulting linear DNA can be re-ligated via the Bgl II restriction enzyme sites flanking the whole rAAV genome.

Figure 5:
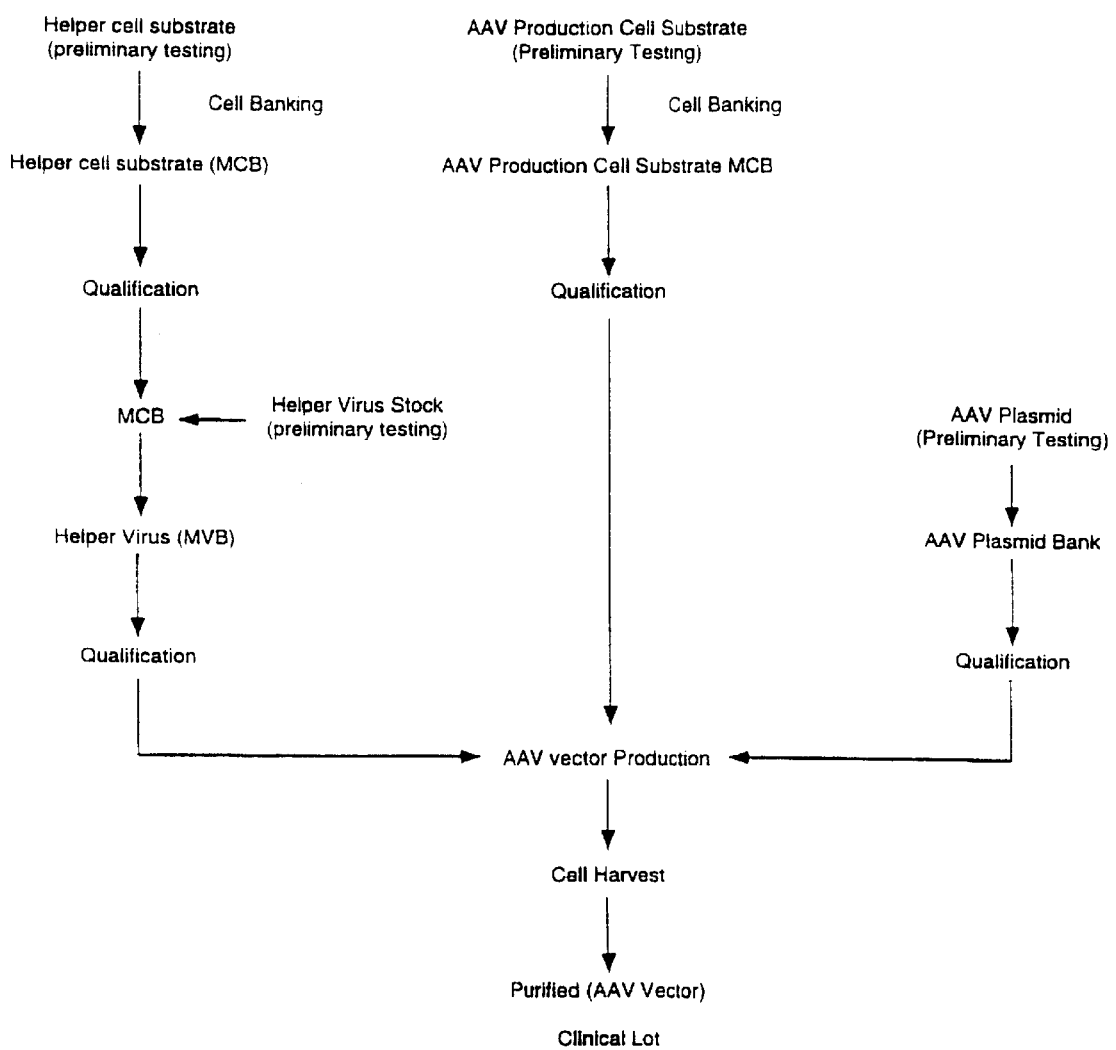

FIG. 5: Production Scheme for AAV

Summary of a scheme for developing AAV packaging cell lines for scalable transient transfection-based rAAV production.

Figure 6:
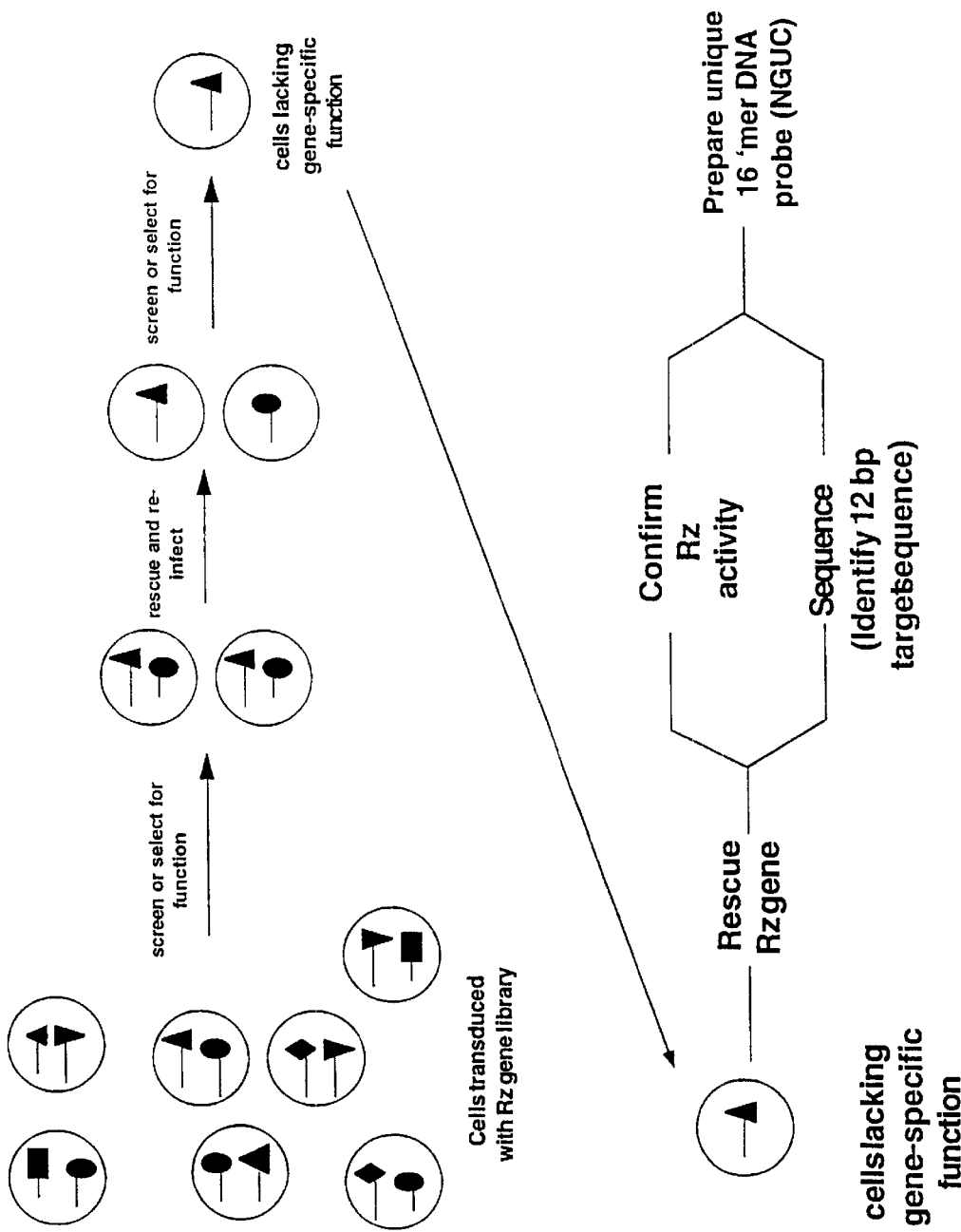

FIG. 6: Concept of Cloning Genes Using AAV-ribozyme Library

Cells are transduced with the AAV-ribozyme library such that each cell expresses one or more ribozymes from the library. The particular phenotype in question is screened and selected for. Positive clones are used to rescue the rAAV responsible followed by re-infection and screening. Once selection is complete, the ribozyme gene is rescued, its activity is confirmed and its sequenced. The deduced sequence is used to prepare a unique DNA probe to clone the target gene.

FIG. 7: Attaching RNA Target to Solid Support

Target RNA can be immobilized on solid supports by a variety of methods, by either their 5' or 3' ends. Details are described in the text.

FIG. 8: In Vitro Selection of Efficient Ribozymes

An in vitro transcribed ribozyme library is applied to the target RNA column under conditions that allow binding but prevent cleavage. Unbound ribozyme are washed away. Conditions are changed to allow cleavage by the bound ribozymes. Active ribozymes are released from the column following successful cleavage. Released ribozyme are amplified, re-synthesized and re-applied to a new column and the process is repeated.

FIG. 9: AAV Stable Integration

Splinkerette assay (Devon et al. (1995) *Nucleic Acids Res.* 23:1644) indicates rAAV is integrating site-specifically in the host cell genome following transduction. Molt 4/8 cells were transduced by AAV AMFT or AMY2 as indicated and selected in G418 until a stable G418 resistant population emerged. DNA was then isolated from uncloned cells and 1 ug DNA was digested with a restriction enzyme that does not cut in the vector so that unintegrated DNA would not be detected. DNA was digested with Bgl II and ligated to oligonucleotide splinkerettes comparable to those previously described (Devon et al. (1995) *Nucleic Acids Res.* 23:1644). PCR was then performed at the indicated Mg++ concentrations using conditions identical to the published procedure. The PCR products were then separated on an agarose gel and probed with a radiolabelled neo probe corresponding to the amplified region of rAAV. Lane 1, 2 Molt 4/8 control; lane 3,4 AMFT.1; lane 5,6 AMFT.2; lane 7,8 AMY2. Note:: AMFT.1 and AMFT.2 are separate transductions with the same vector (AMFT).

FIG. 10: Schematic of Trans Cleavage and Ligation (SEQ ID NOS:9–12)

Auto-catalytic ribozyme library is transcribed in vitro and allowed to self-cleave. Self-cleaved, helix 2-charged ribozymes are purified and incubated with the target RNA. Following cleavage of target, a portion of the charged ribozymes will ligate themselves to the cleavage products. These product-ribozyme species are then amplified by reverse transcription and PCR to yield the target specific ribozymes.

Table 1: AAV Ligation/Transformation Efficiency

Ligation efficiency of ribozyme library gene insert to vector plasmid was determined by counting numbers of bacterial colonies formed after transforming with various amounts of ligated DNA. The data indicate that 1 microgram of ligated DNA can yield $2 \times 10^5$ transformed colonies, which is only 1 log lower that the expected library complexity ($4^{11} = 4.2 \times 10^6$).

Table 2: AAV Transfection Optimization

Transfections were set up with LipofectAmine (GibcoBRL) and DOSPER (Boehringer Mannheim) on A549, HeLa and CF2 cells. Six different volumes of LipofectAmine and DOSPER were tested as well as 3 levels of AAV-NGFR and AdB DNA.

Table 3: High Titer AAV Production

Recombinant AAV preparations with high titers were obtained from current $CsCl_2$ purification procedure. The producer cells were lysed with the non-ionic detergent octylglucoside or the ionic detergent deoxycholate rather than the freeze-thaw procedure used previously. High titer ($5 \times 10^9$ CFU/each preparation) purified rAAV are reproducibly obtained.

Table 4: Optimization of rAAV Stability Following Multiple Freeze/Thaw Steps

Table 5: Optimization of Glycerol Storage Conditions for rAAV

Table 6: Stability of rAAV at 4 Degrees C. in Unclarified Cell Lysates

Table 7: Effect of Benzonase and RQ1 DNase Treatment on rAAV Vector Stability

Table 8: AAV Purification and Concentration

A sample of rAAV-βgal lysate (1.2 column volumes; 10 mg protein) was loaded onto HQ and SP columns hooked-up in tandem and each column was eluted separately with increasing NaCl. HeLa cells were transduced in duplicate with fractions collected during chromatography. Contamination of adenovirus was examined 5 days post-transduction for cytopathic effects (CPE) resulting from adenoviral infection. Titer of rAAV-βgal recovered were measured by staining for βgal activity after transduction.

D. PREFERRED EMBODIMENTS

1. Definitions

Unless defined otherwise, all technical and scientific terms used herein have the same meaning as commonly understood by one of ordinary skill in the art to which this invention belongs. Singleton et al. (1994) Dictionary of Microbiology and Molecular Biology, 2d ed., John Wiley and Sons (New York); Walker (ed.) (1988) The Cambridge Dictionary of Science and Technology, Press Syndicate of the University of Cambridge, NY; and Hale and Marham (1991) The Harper Collins Dictionary of Biology, Harper Perennial, NY, provide one of skill with a general dictionary of many of the terms used in this invention. Paul (1993) Fundamental Immunology, Third Edition Raven Press, New York, N.Y. and the references cited therein provide one of skill with a general overview of the ordinary meaning of many of the virally or immunologically related terms herein. Although any methods and materials similar or equivalent to those described herein can be used in the practice or testing of the present invention, preferred methods and materials are described. For purposes of the present invention, the following terms are defined below.

The term "nucleic acid" refers to deoxyribonucleotides or ribonucleotides and polymers thereof, in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated by the usage of the term, the term nucleic acid is often used interchangeably with gene, cDNA, and mRNA encoded by a gene.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. Unless otherwise indicated, a particular coding nucleic acid sequence also implicitly encompasses conservatively modified variants thereof (e.g. degenerate codon substitutions) and complementary sequences, as well as the sequence explicitly indicated. Specifically, degenerate codon (i.e., different codons which encode a single amino acid) substitutions may be achieved by generating sequences in which the third position of one or more (or all) selected codons is substituted with mixed-base and/or deoxyinosine residues (Batzer et al. (1991) *Nucleic Acid Res.* 19:5081; Ohtsuka et al. (1985) *J. Biol. Chem.* 260:2605–2608; and Cassol et al. (1992); Rossolini et al. (1994) *Mol. Cell. Probes* 8:91–98). Degenerate codons of the native sequence or sequences which may be introduced to conform with codon preference in a specific host cell.

The term "sub-sequence" in the context of a particular reference nucleic acid refers to a region of the nucleic acid smaller than the reference nucleic acid or polypeptide.

"Cellular gene" means a gene usually expressed by the members of a given cell line or cell type without experimental manipulation. It preferably means an endogenous gene that forms part of the cellular genome. Viral genes that may have been integrated into the cellular genome of an ancestral cell and are presently expressed in all cells of a particular cell line are considered "cellular genes". However, the term specifically excludes genes that are expressed in a particular population of cells due to the deliberate experimental infection of that population with selected viruses.

A "ribozyme" is a catalytic RNA molecule which cleaves RNA. The preferred class of ribozymes for the invention is the hairpin ribozyme; hammerheads are specifically not preferred. Preferred hairpin ribozymes cleave target RNA molecules in trans. A ribozyme cleaves a target RNA in vitro when it cleaves a target RNA in solution. A ribozyme cleaves a target RNA in vivo when the ribozyme cleaves a target RNA in a cell. The cell is optionally isolated, or present with other cells, e.g., as part of a tissue, tissue extract, cell culture, or live organism. For example, a ribozyme is active in vivo when it cleaves a target RNA in a cell present in an organism such as a mammal, or when the ribozyme cleaves a target RNA in a cell present in cells or tissues isolated from a mammal, or when it cleaves a target RNA in a cell in a cell culture.

A ribozyme "recognition sequence" or "helix 1" ribozyme domain is the portion of a nucleic acid encoding the ribozyme which is complementary to a target RNA 3' of the cleavage site on the target RNA, i.e., the ribozyme nucleic acid sequences 5' of the ribozyme nucleic acid sub-sequence which aligns with the target cleavage site. A GUC ribozyme typically cleaves an RNA having the sequence NNNBN*GUCNNNNNNNN (SEQ ID NO:14) (where N*G is the cleavage site, B is any of G, U or C, and where N is any of G, U, C, or A). GUA ribozymes typically cleave an RNA target sequence consisting of NNNNN*GUANNNNNNNN. (where N*G is the cleavage site and where N is any of G, U, C, or A). A "GUA site" is an RNA sub-sequence which includes the nucleic acids GUA which is cleaved b a GUA ribozyme. A "GUC site" is an RNA sub-sequence which includes the nucleic acids GUC which is cleaved by a GUC ribozyme.

A library of hairpin ribozyme-encoding nucleic acids denotes a collection of nucleic acids wherein every possible recognition sequence is represented. In other words, the nucleotide residue at each position of the recognition sequence other than the GUA or GUC site can be a G, U, C, or A (collectively referred to by an "N", see previous example and FIG. 1).

The term "isolated", when applied to a nucleic acid or protein, denotes that the nucleic acid or protein is essentially free of other cellular components with which it is associated in the natural state. In particular, an isolated gene of interest is separated from open reading frames which flank the gene and encode a gene product other than that of the specific gene of interest. A "purified" nucleic acid or protein gives rise to essentially one band in an electrophoretic gel, and is at least 85% pure, more preferably at least 95% pure, and most preferably at least 99% pure.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers (1981) Tetrahedron Lett. 22:1859–1862, or by the triester method according to Matteucci et al. (1981) J. Am. Chem. Soc., 103:3185, both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of, for example, total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al. (1989) Molecular Cloning: A Laboratory Manual (2d ed.), Vols. 1–3, Cold Spring Harbor Laboratory (hereinafter, Sambrook et al.) or F. Ausubel et al. (ed.) (1987) Current Protocols in Molecular Biology, Greene Publishing and Wiley-Interscience, New York (1987).

A "promoter" is an array of cis-acting nucleic acid control sequences which direct transcription of an associated nucleic acid. As used herein, a promoter includes nucleic acid sequences near the start site of transcription, such as a polymerase binding site. The promoter also optionally includes distal enhancer or repressor elements which can be located as much as several thousand base pairs from the start site of transcription. A "constitutive" promoter is a promoter which is active under most environmental conditions and states of development or cell differentiation, such as a pol III promoter. An "inducible" promoter initiates transcription in response to an extracellular stimulus, such as a particular temperature shift or exposure to a specific chemical.

A "pol III promoter" is a DNA sequence competent to initiate transcription of associated DNA sequences by pol III. Many such promoters are known, including those which direct expression of known t-RNA genes. A general review of various t-RNA genes can be found in Watson et al. MOLECULAR BIOLOGY OF THE GENE Fourth Edition, The Benjamin Cummings Publishing Co., Menlo Park, Calif. pages 710–713.

A nucleic acid of interest is "operably linked" to a promoter, vector or other regulatory sequence when there is a functional linkage in cis between a nucleic acid expression control sequence (such as a promoter, or array of transcription factor binding sites) and the nucleic acid of interest. In particular, a promoter that is operably linked to a nucleic acid of interest directs transcription of the nucleic acid.

A regulatory nucleic acid is one that initiates, causes, enhances or inhibits the expression of a particular selected nucleic acid or gene product, either directly or through its gene product. Examples of trans-acting regulatory nucleic acids includes nucleic acids that encode initiators, inhibitors and enhancers of transcription, translation, or post-transcriptional (e.g., RNA splicing factors) or post translational processing factors, kinases, proteases An "expression vector" includes a recombinant expression cassette which has a nucleic acid which encodes an RNA that can be transcribed by a cell. A "recombinant expression cassette" is a nucleic acid construct, generated recombinantly or synthetically, with a series of specified nucleic acid elements which permit transcription of an encoded nucleic acid in a target cell. The expression vector can be part of a plasmid, virus, or nucleic acid fragment. Typically, the recombinant expression cassette portion of an expression vector includes a nucleic acid to be transcribed, and a promoter. In some embodiments, the expression cassette also includes, e.g., an origin of replication, and/or chromosome integration elements such as retroviral LTRs, or adeno associated viral (AAV) ITRs.

The phrase "exogenous," "genetically engineered" or "heterologous nucleic acid" generally denotes a nucleic acid that has been isolated, cloned and ligated to a nucleic acid with which it is not combined in nature, and/or introduced into and/or expressed in a cell or cellular environment other than the cell or cellular environment in which said nucleic acid or protein may typically be found in nature. The term encompasses both nucleic acids originally obtained from a different organism or cell type than the cell type in which it is expressed, and also nucleic acids that are obtained from the same cell line as the cell line in which it is expressed. The term also encompasses a nucleic acid indicates that the nucleic acid comprises two or more subsequences which are not found in the same relationship to each other in nature. For instance, the nucleic acid is typically recombinantly produced, having two or more sequences derived from unrelated genes arranged to make a new functional nucleic acid. For example, in one embodiment, the nucleic acid has a promoter from one gene, such as a human t-RNA gene, arranged to direct the expression of a coding sequence from a different gene, such as an artificial gene coding for a ribozyme. When used with reference to a ribozyme, the term "heterologous" means that the ribozyme is expressed in a cell or location where it is not ordinarily expressed in nature, such as in a T cell which encodes the ribozyme in an expression cassette.

The term "recombinant" or "genetically engineered" when used with reference to a nucleic acid or a protein generally denotes that the composition or primary sequence of said nucleic acid or protein has been altered from the naturally occurring sequence using experimental manipulations well known to those skilled in the art. It may also denote that a nucleic acid or protein has been isolated and cloned into a vector or a nucleic acid that has been introduced into or expressed in a cell or cellular environment, particularly in a cell or cellular environment other than the cell or cellular environment in which said nucleic acid or protein may be found in nature.

The term "recombinant" or "genetically engineered" when used with reference to a cell indicates that the cell replicates or expresses a nucleic acid, or produces a peptide or protein encoded by a nucleic acid, whose origin is exogenous to the cell. Recombinant cells can express nucleic acids that are not found within the native (nonrecombinant) form of the cell. Recombinant cells can also express nucleic acids found in the native form of the cell wherein the nucleic acids are re-introduced into the cell by artificial means.

A cell has been "transduced" by an exogenous nucleic acid when such exogenous nucleic acid has been introduced inside the cell membrane. Exogenous DNA may or may not be integrated (covalently linked) into chromosomal DNA making up the genome of the cell. The exogenous DNA may be maintained on an episomal element, such as a plasmid. In eukaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eukaryotic cell to establish cell lines or clones comprised of a population of daughter cells containing the exogenous DNA.

A vector "transduces" a cell when it transfers nucleic acid into the cell. A cell is "stably transduced" by a nucleic acid when a nucleic acid transduced into the cell becomes stably replicated by the cell, either by incorporation of the nucleic acid into the cellular genome, or by episomal replication. A vector is "infective" when it transduces a cell, replicates, and (without the benefit of any complementary vector) spreads progeny vector of the same type as the original transducing vector to other cells in an organism or cell culture, wherein the progeny vectors have the same ability to reproduce and spread throughout the organism or cell culture.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

A "transgene" comprises a nucleic acid sequence used to form a chimeric or transgenic animal when introduced into the chromosomal material of the somatic and germ line cells of a non-human animal by way of human intervention, such as by way of the methods described herein to form a transgenic animal. The particular embodiments of the transgenes of the invention are described in more detail hereinafter.

An "embryonic target cell" is a cell into which the transgenes of the invention are introduced to produce "chimeric" animals (wherein only a subset of cells is transduced) or "transgenic" non-human animals (wherein every cell is transduced). Examples include embryonic stem (ES) cells, or preferably the fertilized oocyte (zygote). In some cases, chimeric animals can also be produced by isolating stem cells from an animal, transducing them in vitro, and reinfusing them into the original donor or into an allogeneic recipient.

"Expresses" denotes that a given nucleic acid comprising an open reading frame is transcribed to produce an RNA molecule. It also denotes that a given nucleic acid is transcribed and translated to produce a polypeptide. "Gene product" refers to the RNA produced by transcription or to the polypeptide produced by translation of a nucleic acid.

"Cloning a cell" denotes that a single cell is proliferated to produce a genetically and phenotypically homogeneous population of progeny cells descended from the single cell.

"Phenotype" denotes a definable detectable heritable trait of a cell or organism, that is caused by the presence and action at least one gene.

A "ligand" is a molecule or chemical compound that detectably and selectively binds to a reference molecule but not to other molecules, preferably with an affinity higher than $10^{-3}$ M, more preferably greater than $10^{-5}$ M, and most preferably about $10^{-7}$ or higher.

"Sensitivity to a selected chemical compound" means that exposure to a particular chemical compound reproducibly causes a cell to alter its metabolism in predictable ways, e.g. by inducing slower growth, apoptosis, proliferation, induction o or shutdown of certain genes, etc.

"Packaging" or "packaged" denotes that a specific nucleic acid or library is contained in and operably linked to a defined vector, such as an adenovirus associated vector.

2. Detailed Description of the Invention

A principal objective of this invention is to use a "library" of ribozyme genes containing all possible target recognition sequences to identify, isolate and/or characterize known and unknown genes that encode detectable phenotypic traits. It is also an object to use the library to selectively ablate known and unknown genes, preferably in vivo.

To practice the methods of the present invention, it is necessary to produce a library of nucleic acids which encode hairpin ribozymes with randomized or pseudo-randomized recognition sequences. This library is then inserted into a vector of choice; the particular vector may differ as a function of the application.

Several different types of ribozymes have been discovered and applied (for review see Cech and Bass (1986) *Ann. Rev. Biochem* 55:599; Kijima et al. (1995) *Pharmac. Ther.* 68:247). However, hairpin ribozymes are superior for a number of non-obvious reasons, described below.

In generating a random ribozyme library, the most critical considerations are 1) the generation of a library with sufficient complexity to assure the presence of ribozymes uniquely specific for any and all given targets, and 2) the competence to package and express, as nearly as possible, the complete library. At the same time, the library must be small enough for it to be technically feasible to make, maintain, and reproducibly manipulate and use.

However, given current technical capabilities, the synthesis, cloning into viral vectors and efficient delivery into cells of a complex library is not trivial. The more complex the library (i.e., the greater the number of individual ribozyme species), the more difficult it is to clone the complete library into a vector. As an example, a ribozyme library useful for identifying and targeting a gene within the human genome (estimated between 1 to $3 \times 10^9$ base pairs) would require a ribozyme library of sufficient complexity to recognize any gene in the genome. In order to achieve a suitable degree of binding specificity, the target recognition site of the ribozyme should contain at least about 15 to 16 specific nucleotides. A completely randomized recognition sequence of this size would comprise $4^{15}=1.1 \times 10^9$ to $4^{16}=4.3 \times 10^9$ different ribozyme species. Due to the inefficiencies of ribozyme-vector ligation, cell transfection, viral vector titer, etc. creating a usable library containing 1 to $4 \times 10^9$ different ribozyme molecules and expressing the entire library in a population of transformed cells would be difficult, if not technically impossible.

Fortunately, the hairpin ribozyme is unique in its requirement for a GUC or GUA within the target site. Due to this requirement, constructing a library with 15 specific nucleotides (to continue the example described above) requires only 12 random nucleotides, to recognize a substrate in the form: 5'-NNNNXGUCNNNNNNNN-3' or 5'-NNNNXGUA NNNNNNN-3' (the underlined regions indicate basepairs formed with the ribozyme, where N=A,C,G or T and position X has no restrictions and does not interact with the substrate). Such a hairpin ribozyme library has a complexity of $4^{12}$ ($1.7 \times 10^7$) different ribozyme genes or molecules. In comparison, a library of hammerhead ribozymes having a recognition sequence of 15 nucleotides comprises about $10^9$ different species, which have fewer (if any) stringent sequence requirements in the target (Akhtar et al. (1995) *Nature Medicine*, 1:300; Thompson et al. (1995) *Nature Medicine* 1:277; Bratty et al. (1993) *Biochim. Biophys. Acta.*, 1216:345; Cech and Uhlenbeck (1994) *Nature* 372:39; Kijima et al. (1995) *Pharmac. Ther.*, 68:247). In other words, a hammerhead library involving a 15 nucleotide recognition site would require 64 times more individual ribozyme molecules than a hairpin library involving a recognition sequence of equal size. This is a substantial difference. For this reason, constructing a hairpin ribozyme library, packaging it into a vector, and expressing the entire library in transformed cells is considerably more technically feasible than constructing a similar hammerhead library.

Another advantage that hairpin ribozymes have over hammerhead ribozymes is their intrinsic stability and folding in vivo. The secondary structure of a hammerhead ribozyme, not bound to a target, consists of one helix that is only 4 nucleotides in length which is unlikely to remain intact at physiological temperature, 37° C. (Akhtar et al. (1995) *Nature Medicine*, 1:300; Thompson et al. (1995) *Nature Medicine* 1:277; Bratty et al. (1993) *Biochim. Biophys. Acta.*, 1216:345; Cech and Uhlenbeck (1994) *Nature* 372:39; Kijima et al. (1995) *Pharmac. Ther.* 68:247). Indeed, the crystal structure of the hammerhead could only be solved when it was bound to a DNA or RNA substrate (Pley et al. (1994) *Nature* 372:68; Scott et al. (1995) *Cell* 81:991), suggesting that the hammerhead ribozyme does not have a stable structure prior to substrate binding. In contrast, the hairpin ribozyme contains two helices totaling 7 nucleotides (FIG. 1), thus making it more stable under physiological temperatures and in the intracellular milieu which contains, among other things, RNases that can more effectively cleave RNAs lacking secondary structure. Furthermore, since the hairpin ribozyme has a more stable secondary structure prior to binding substrate, it would be less likely to improperly fold or interact with flanking sequences in the ribozyme RNA transcript. Sequences comprising a hammerhead riboyzme, however, would be free to interact with any extraneous sequences in the transcript resulting in the inactivation of the ribozyme.

Another advantage that hairpin ribozymes have over hammerhead ribozymes is that the cleavage success rate of any given target sequence is higher for the hairpin ribozyme than for the hammerhead. This conclusion has been reached empirically, but can also be explained based on the difference between the two ribozymes' target requirements. The hammerhead ribozyme is very promiscuous, requiring minimal sequence in the target (see above references). Due to its high promiscuity, it has a relatively low success rate when given a variety of potential sites. Conversely, the hairpin ribozyme has significantly more stringent requirements, where its substrate must contain a GUC. Due to the relative rarity of potential sites, the hairpin ribozyme has necessarily developed a higher success rate for cleavage. Indeed, nearly all (>90%?) of the potential ribozyme sites we have tested thus far have been cleavable by the appropriate hairpin ribozyme (U.S. applications Ser. Nos. 08/664,094; 08/719,953).

Additionally, one of the applications of our hairpin ribozyme library is the generation of target-specific libraries (discussed in detail in section 2.h). One method uses the inherent ability of hairpin ribozymes to catalyze a trans-ligation reaction between cleavage products. This ligation capability is significantly more active in the hairpin ribozyme than in the hammerhead (Berzal-Herranz et al (1992) Genes and Development 6:1).

Finally, it has been determined empirically that the hairpin ribozyme functions optimally under physiological levels of magnesium (Chowria et al. (1993) *Biochemistry* 32:1088) and temperature (37° C.), whereas the hammerhead performs optimally at higher magnesium and temperature (Bassi et al. (1996) *RNA* 2:756; Bennett et al. (1992) *Nucleic Acids Research* 20:831). These observations become significant when developing and delivering ribozymes in vivo and indicate a clear advantage for hairpin ribozymes.

a. Making and Maintaining Libraries of Hairpin Ribozyme-encoding Nucleic Acids Having Randomized Recognition Sequences Construction of a library that encodes hairpin ribozyme genes having randomized recognition sequences typically involves:

1) Synthesizing nucleic acids which encode hairpin ribozymes having randomized recognition sequences using oligonucleotides randomized in the helix 1 and helix 2 regions of the ribozyme; the ribozyme libraries are generated including 6, 7, 8, 9, or 10 bases in the helix 1 region of the ribozyme gene;
2) Inserting the library into an appropriate vector;
3) transforming suitable cells (e.g., *E. coli*) to amplify the library;
4) purification of the amplified library;
5) packaging the library into expression vectors that efficiently transfect suitable target cells (e.g. HeLa or A549 cells; although adeno-associated viral vectors are preferred for ribozyme library gene cloning, others may be used).

i. Synthesis of Randomized Ribozyme Genes

Synthesis of ribozyme-encoding nucleic acids with randomized sequences may be accomplished by any one of a number of methods known to those skilled in the art. See, e.g., Oliphant et al. (1986) *Gene* 44:177–183; U.S. Pat. Nos. 5,472,840, and 5,270,163. In one approach, the entire ribozyme-encoding nucleic acid is chemically synthesized by known methods one nucleotide at a time, for example in an ABI 380B synthesizer. Whenever it is desired that a given position be randomized, all four nucleotide monomers are added to the reaction mixture. After synthesis, the end-products are sequenced by any method known in the art to confirm that the catalytic backbone of the hairpin ribozyme is invariant, and that the recognition sequence is randomized.

In another approach, a randomized oligonucleotide is spliced to the catalytic region of the hairpin ribozyme. This avoids having to chemically synthesize the entire ribozyme.

It should be noted that synthesis and delivery of ribozyme genes rather than RNA ribozymes per se is preferred in the present invention because: ribozyme genes allow for the constant and continuous production of ribozymes, the ribozyme gene is effectively delivered to the intracellular site of action, and stable gene delivery enables genetic selection of the loss of certain cell functions. The randomized library preferably includes at least $10^5$ ribozyme genes; the upper limit ($10^8$, $10^9$ or more) depends on the number of residues in the recognition site.

ii. Insertion of Randomized Ribozyme Genes into a Cloning or Expression Vector

Once the ribozyme library is generated, it is packaged into a cloning or expression vector by methods known in the art, and the packaged library is cloned into suitable cells and amplified. Although cloning and amplification are typically accomplished using bacterial cells, any combination of cloning vector and cell may be used. The cloned cells can be frozen for future amplification and use, or the packaged library can be isolated and itself stored frozen or in lyophilized form.

Typical cloning vectors contain defined cloning sites, origins of replication and selectable genes.

Expression vectors typically further include transcription and translation initiation sequences, transcription and translation terminators, and promoters useful for regulation of the expression of the particular nucleic acid. Expression vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Additionally, the vectors contain a nuclear processing signal, appropriate spicing signals and RNA stability sequences and/or structures (e.g. stable stem-loops, etc.) at either 5' or 3' or both ends, all of which will be present in the expressed ribozyme RNA transcript. Vectors are suitable for replication and integration in prokaryotes, eukaryotes, or preferably both. For general descriptions of cloning, packaging, and expression systems and methods, see Giliman and Smith (1979) *Gene* 8:81–97; Roberts et al. (1987) *Nature* 328:731–734; Berger and Kimmel (1989) Guide to Molecular Cloning Techniques, Methods in Enzymology, Vol. 152, Academic Press, Inc., San Diego, Calif, (Berger); Sambrook et al. (1989) Molecular Cloning—A Laboratory Manual (2nd ed.) Vols. 1–3, Cold Spring Harbor Laboratory, Cold Spring Harbor Press, N.Y., (Sambrook); and F. M. Ausubel et al. (eds.) (1994) Current Protocols in Molecular Biology, Current Protocols, a joint venture between Greene Publishing Associates, Inc. and John Wiley & Sons, Inc. (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill. Particular expression vectors are discussed in greater detail below.

The nucleic acids (e.g., promoters, vectors, and coding sequences) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al. (1981) *Tetrahedron Lett.* 22:1859–1862; Matteucci et al. (1981) *J. Am. Chem. Soc.* 103:3185–3191; Caruthers, et al . (1982) *Genetic Engineering* 4:1–17; Jones, chapter 2, Atkinson, et al., chapter 3, and Sproat, et al., chapter 4, in Gait (ed.) (1984) Oligonucleotide Synthesis: A Practical Approach, IRL Press, Washington D.C.; Froehler, et al. (1986) *Tetra-* hedron Lett. 27:469–472; Froehler et al. (1986) *Nucleic Acids Res.* 14:5399–5407; Sinha, et al. (1983) *Tetrahedron Lett.* 24:5843–5846; and Sinha, et al. (1984) *Nucl. Acids Res.* 12:4539–4557, which are incorporated herein by reference.

b. Expression of the Ribozyme Gene Library

Once made, the ribozyme library is expressed in a variety of recombinantly engineered cells and organisms.

i. Cells to Be Transduced

The compositions and methods of the present invention are used to transfer nucleic acids, particularly ribozyme-encoding nucleic acids, into a wide variety of cell types, in vivo and in vitro. For in vitro applications, the delivery of nucleic acids can be to any cell that can be grown or maintained in culture, whether of bacterial, plant or animal origin, vertebrate or invertebrate, and of any tissue or type. Although any prokaryotic or eukaryotic cells may be used, the preferred cell will be one in which the target gene is normally expressed (i.e. liver cells for liver-specific genes, tumor cells for oncogenes, etc.) or has been caused to be expressed. Furthermore, the cell would preferably contain a reporter or sortable gene to expedite the selection process.

The culture of cells is well known in the art. Freshney (1994) Culture of Animal Cells, A Manual of Basic Technique, (3d ed.) Wiley-Liss, New York; Kuchler et al. (1977) Biochemical Methods in Cell Culture and Virology, Kuchler, R. J., Dowden, Hutchinson and Ross, Inc., and the references cited therein provide a general guide to the culture of cells. Cultured cell systems often will be in the form of monolayers of cells, although cell suspensions are also used.

ii. Transduction Methods

There are several well-known methods of introducing nucleic acids into bacterial, animal or plant cells, any of which may be used in the present invention. These include: calcium phosphate precipitation, fusion of the recipient cells with bacterial protoplasts containing the nucleic acid, treatment of the recipient cells with liposomes containing the nucleic acid, DEAE dextran, receptor-mediated endocytosis, electroporation, micro-injection of the nucleic acid directly into the cells, infection with viral vectors, etc. Cationic liposomes-mediated delivery of AAV-ribozyme-library provector plasmid may be employed (Philp et al. (1994) *Mol. Cell. Biol.* 14:2411–2418).

Contact between the cells and the genetically engineered nucleic acid constructs, when carried out in vitro, takes place in a biologically compatible medium. The concentration of nucleic acid varies widely depending on the particular application, but is generally between about 1 micromolar and about 10 millimolar. Treatment of the cells with the nucleic acid is generally carried out at physiological temperatures (37° C.) for periods of time of from about 1 to 48 hours, preferably of from 4 to 12 hours. For viral transduction, cells are incubated with vector at an appropriate multiplicity of infection (m.o.i.)(depends on application, see below) for 4 to 16 hours (Flotte et al. (1994) *Am. J. Resp. Cell Mol. Biol.* 11:517).

In one group of embodiments, a nucleic acid is added to 60–80% confluent plated cells having a cell density of from about $10^3$ to about $10^5$ cells/mL, more preferably about $2\times10^4$ cells/mL. The concentration of the suspension added to the cells is preferably of from about 0.01 to 0.2 micrograms/mL, more preferably about 0.1 micrograms/mL.

iii. Reporter Genes Which May be Used

A reporter gene (also, marker gene) is one whose gene product is readily inducible and/or detectable, that is used to detect cells that are transduced with a vector that encodes the reporter gene, to isolate and clone such cells, and to monitor the effects of environmental and cytoplasmic factors on gene expression in the transduced cells. Preferred reporter genes are those that render cells FACS-sortable: e.g., genes for fluorescent proteins, including green fluorescent protein (GFP) and any mutant thereof; nerve growth factor receptor (NGFR) and any mutant thereof; genes for cell surface proteins that may be coupled to easily detected ligands such as fluorescent antibodies. Specific reporter genes that can be selected for or against in tissue culture, which may be used herein include the hprt gene (Littlefield (1964) *Science* 145:709–710), the tk (thymidine kinase) gene of herpes simplex virus (Giphart-Gassler et al. (1989) *Mutat. Res.* 214:223–232), the nDtll gene (Thomas et al. (1987) *Cell* 51:503–512; Mansour et al. (1988) *Nature* 336:348–352), or other genes which confer resistance or sensitivity to amino acid or nucleoside analogues, or antibiotics, etc.

For the most part, reporter genes are used herein to identify cells that have been transduced with nucleic acids that encode a ribozyme and or a gene of interest. It is possible that a given cell clone identified as under-expressing the reporter gene may contain a ribozyme gene that cleaves the gene product of the reporter gene instead of the gene of interest, in which case the ribozyme genes. against the reporter gene will be mis-identified as ribozymes directed against the gene of interest. Thus, it is preferable to generate a cell line that co-expresses at least two or three different reporter genes linked to the gene of interest. Only ribozyme genes that inhibit the gene of interest will result in under-expression of more than one reporter gene simultaneously. Alternatively, it may be necessary to pre-screen the library to ensure that the reporter RNA is not the target of the ribozyme attack. In addition, pre-screening may also be required to ensure that the presence of any reporter RNA does not alter accessibility or structure of the target RNA.

iv. Vectors Useful for Maximal Ribozyme Expression

A number of viral vector systems can be used to express ribozyme libraries in viva, including retroviral vectors, vaccinia vectors, herpes simplex vectors, Sindbis/semliki forest viruses, adenoviral vectors, and adeno-associated viral (AAV) vectors. Each vector system has advantages and disadvantages, which relate to host cell range, intracellular location, level and duration of transgene expression and ease of scale-up/purification. Optimal delivery systems are characterized by: 1) broad host range; 2) high titer/μg DNA; 3) stable expression; 4) non-toxic to host cells; 5) no replication in host cells; 6) ideally no viral gene expression; 7) stable transmission to daughter cells; 8) high rescue yield; and 9) lack of subsequent replication-competent virus that may interfere with subsequent analysis. Choice of vector may depend on the intended application.

(a) AAV Vectors

Because of their demonstrated ease of use, broad host range, stable transmission to daughter cells, high titer/microg DNA, and stable expression, (Lebkowski et al. (1988) *Mol. Cell. Biol.* 8:3988–3996), adeno-associated viral vector are preferred to deliver ribozyme library genes into target cells. See, e.g., D. V. Goeddel (ed.) (1990) *Methods in Enzymology, Vol.* 185, Academic Press, Inc., San Diego, Calif. or M. Krieger (1990) Gene Transfer and Expression—A Laboratory Manual, Stockton Press, New York, N.Y., and the references cited therein. AAV requires helper viruses such as adenovirus or herpes virus to achieve productive infection.

AAV displays a very broad range of hosts including chicken, rodent, monkey and human cells (Muzycka, N., 1992 Curr. Top. Microbiol. Immunol. 158, 97–129; Tratschin et al., 1985, Mol. Cell. Biol. 5:3251–3260; Lebkowski et al., 1988. Mol. Cell. Biol. 8:3988–3996. They efficiently transduce a wide variety of dividing and non-dividing cell types in vitro (Flotte, T. R, et al., 1992. Am. J. Respir. Cell. Mol. Biol. 7, 349–356; Podsakoff, G. et al. 1994. J. Virol. 68 5655–5666, Alexander, I. Z. et al, 1994 J. Virol, 68, 8282–8287). AAV vectors have been demonstrated to successfully transduce hematopoietic progenitor cells of rodent or human origin (Nahreini, Py et al., 1991, Blood, 78:2079). It is believed that AAV could virtually infect any mammalian cell type.

Moreover, the copy number for the neo gene introduced by the AAV vector is more than 2 orders of magnitude higher than that of retrovirally-transduced human tumor-infiltrating lymphocyte (TIL) cell cultures. Long-term in vivo gene expression has recently been demonstrated in the lungs of rabbit and primates that received AAV-CFTR vector in a local pulmonary administered for up to six months (Conrad, C. K., et al. 1996. Gene Therapy 3, 658–668). Administration of the AAV-CFTR gene product resulted in consistent gene transfer, and persistence of the gene in one human parent out to 70 days (10th Annual North American Cystic Fibrosis Conference, Orlando, Fla., Oct. 25–27, 1996).

Integration is important for stable transgene expression, especially in cells that are actively dividing. Site-specific integration is even better since there is less chance of disrupting a cellular gene, less chance of inactivating the target gene by the insertion and it lends itself to more consistent expression of the delivered transgene. In the absence of helper virus functions, AAV integrates (site-specifically) into a host cell's genome. The integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993) *Current Opinion in Genetic and Development* 3:74–80, and the references cited therein provides an overview of the AAV life cycle. See also West et al. (1987) *Virology* 160:38–47; Carter et al. (1989) U.S. Pat. No. 4,797,368; Carter et al. (1993) WO 93/24641; Kotin (1994) *Human Gene Therapy* 5:793–801; Muzyczka (1994) *J. Clin. Invest.* 94:1351 and Samulski, supra, for an overview of AAV vectors.

Although wild-type AAV reportedly integrates efficiently at a specific site on chromosome 19 (Kotin R M, et al., *Proc Natl Acad Sci USA* 1990; 87 2211–2215; Kotin R M, et al. EMBO J 1992, 11:5071–5078; Samulski R J et al. EMBO J 1991, 10:3941–3950 Samulski R J, Curr Opin Biotech 1993, 3:74–80) recent evidence indicates that rep-deleted AAV vectors do not integrate with any appreciable efficiency or specificity. Flotte T R et al. (1994) *Am J. Resp Cell Mol Biol* 11:517–521; Kearns et al. (1996) *Gene Therapy* 3:748; Fisher-Adams et al. (1996) *Blood* 88:492). Data generated using Southern and fluorescent in situ hybridization (FISH) analyses, indicates that rAAV integrates into a finite number of chromosomal sites, possibly hot spots for recombination.

Once a cell or cells have been selected and shown to contain the ribozyme(s) of interest, the entire AAV-ribozyme expression cassette can be easily "rescued" from the host cell genome and amplified by introduction of the AAV viral proteins and wild type adenovirus (Hermonat P. L. and N. Muzyczka (1984) *PNAS. USA* 81:6466–6470; Tratschin, J. et al. (1985) *Mol. Cell. Biol.* 5:3251–3260; Samulski, R. J. et al (1982) *PNAS USA* 79:2077–2081; Tratschin et al. (1985) *Mol. Cell. Biol.* 5:3251–3260). This makes isolation, purification and identification of selected ribozymes considerably easier than other molecular biology techniques.

In order to ensure that there is no loss of complexity in packaging the ribozyme library, the complexity of the ribozyme library is monitored as follows:

Cells expressing an HSV-tk gene or transduced with an pHSV-TK gene are transduced with either an AAV vector or an AAV-ribozyme-Lib vector, and cultured in the presence of gancyclovir and G418. Cells that lack a functional ribozyme that cleaves the tk mRNA will express thymidine kinase and die. Cells that inactivate the HSV tk gene product with one or more specific ribozymes will survive. Surviving cells are amplified, and the sequence of the anti-HSV tk ribozyme is determined by PCR of ribozyme gene(s), followed by sequencing analysis of the amplified product. The ribozyme gene sequences that are complementary to regions of the tk gene sequence can be used as a gene probe for HSV tk gene. Once ribozymes that appear to inactive tk have been isolated, their catalytic activity can be verified by converting them into "disabled" ribozymes (i.e. disrupting their catalytic activity without affecting substrate binding, see section 2.h. How to distinguish between ribozyme effects . . . above for a more detailed description) followed by re-analyzing their effects in vivo.

Alternatively, cells expressing any other selectable or FACS-sortable marker, such as green fluorescent protein (GFP) or Erb, can also be used as the target for testing the complexity of the invented AAV-ribozyme library vector.

(b) Retroviral Vectors

Retroviral vectors may also be used in certain applications. The design of retroviral vectors is well known to one of skill in the art. See Singer, M. and Berg, P., supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712; Gilboa (1986) *Biotechniques* 4:504–512, Mann et al. (1983) *Cell* 33:153–159; Cone and Mulligan (1984) *Proc. Natl. Acad. Sci. USA* 81:6349–6353, Eglitis et al. (1988) *Biotechniques* 6:608–614; Miller et al. (1989) *Biotechniques* 7:981–990; Miller, A. D. (1992) *Nature*, supra; Mulligan, R. C. (1993) supra; and Gould et al., and International Patent Application No. WO 92/07943 entitled "Retroviral Vectors Useful in Gene Therapy." The teachings of these patents and publications are incorporated herein by reference.

The retroviral vector particles are prepared by recombinantly inserting a nucleic acid encoding a nucleic acid of interest into a retrovirus vector and packaging the vector with retroviral capsid proteins by use of a packaging cell line. The resultant retroviral vector particle is generally incapable of replication in the host cell and is capable of integrating into the host cell genome as a proviral sequence containing the calbindin nucleic acid. As a result, the host cell produces the gene product encoded by the nucleic acid of interest.

Packaging cell lines are generally used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transducing a cell line with one or more expression plasmids encoding the appropriate core and envelope proteins. In these cells, the gag, pol, and env genes can be derived from the same or different retroviruses.

A number of packaging cell lines suitable for the present invention are available in the prior art. Examples of these cell lines include Crip, GPE86, PA317 and PG 13. See Miller et al. (1991) *J. Virol.* 65:2220–2224, which is incorporated herein by reference. Examples of other packaging cell lines are described in Cone, R. and Mulligan, R. C. (1984) *Proceedings of the National Academy of Sciences, U.S.A.* 81:6349–6353 and in Danos, O. and R. C. Mulligan (1988) *Proceedings of the National Academy of Sciences, U.S.A.* 85:6460–6464; Eglitis et al. (1988) *Biotechniques* 6:608–614; Miller, A. D. et al. (1989) *Biotechniques* 7:981–990, also all incorporated herein by reference. Amphotropic or xenotropic envelope proteins, such as those produced by PA317 and GPX packaging cell lines may also be used to package the retroviral vectors.

Although retroviral vectors (RVV) have been used extensively in the past, and could be used to deliver our ribozyme gene library, they are not the vector of choice for several reasons: 1) it is difficult to produce and purify RVV to high titer, 2) the virus is enveloped and therefore is relatively unstable during storage or freeze/thaw, 3) RVV genomes are positive strand RNA, which would be a target for ribozymes in the library and 4) while they do stably integrate into the host genome, the integration step requires one round of cell division, which could be problematic when delivering is in vivo or to non-dividing cells.

(c) Sindbis/Semliki Forest Viruses

Sindbis/semliki forest viruses (Berglund et al. (1993) *Biotechnology* 11:916–920) are positive-strand RNA viruses that replicate in the cytoplasm, are stably maintained, and can yield very high levels of antisense RNA. Sindbis vectors are thus a third type of vector useful for maximal utility.

v. Promoters Useful for Ribozyme Expression

The promoters used to control the gene expression from AAV include: (a) viral promoters such as SV40, CMV, retroviral LTRs, herpes virus TK promoter, parvovirus B-19 promoter (Muzycka, N, 1992, *Curr. Top. Microbiol. Immunol.* 158, 97–129), AAV p5 and p40 promoters (Tratschin, J. D., et al., 1993. *Am. J. Respir. Cell. Mol. Biol.* 7, 349–356). (b) human gene promoters such as the gamma-globin promoter (Walsh, C. F. et al., 1992, *Proc. Nat. Acad. Sci,, USA* 89, 7257–7261) or the β-actin promoter; and (c) RNA pol III promoters such as cellular tRNA promoters or the promoter from the adenovirus VA1 gene (U.S. application Ser. No. 08/664,094; U.S. application serial No. 08/719,953)

vi. Detection of Nucleic Acid Presence and Expression

A number of embodiments of the present invention require detecting and quantifying specific nucleic acids, such as specific genes, RNA transcripts or ribozymes. A variety of methods for specific DNA and RNA detection and measurement, many involving nucleic acid hybridization techniques, are known to those of skill in the art. See Sambrook, et al.; Hames and Higgins (eds.) (1985) Nucleic Acid Hybridization, A Practical Approach, IRL Press; Gall and Pardue (1969) *Proc. Natl. Acad. Sci. USA*, 63:378–383; and John et al. (1969) *Nature* 223:582–587. The selection of a particular hybridization format is generally not critical.

Hybridization is carried out using nucleic acid probes which are designed to be complementary to the nucleic acid sequences to be detected. The probes can be full length or less than the full length of the target nucleic acid. Preferably nucleic acid probes are 20 bases or longer in length. Shorter probes are empirically tested for specificity. (See Sambrook, et al. for methods of selecting nucleic acid probe sequences for use in nucleic acid hybridization.)

For example, desired nucleic acids will hybridize to complementary nucleic acid probes under the hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Oligonucleotides for use as probes are chemically synthesized, for example, according to the solid phase phosphoramidite triester method first described by Beaucage, S. L. and Carruthers, M. H., 1981, *Tetrahedron Lett.,* 22(20):1859–1862 using an automated synthesizer, as described in Needham-VanDevanter, D. R., et al., 1984, *Nucleic Acids Res.,* 12:6159–6168. Purification of oligonucleotides is by either native acrylamide gel electrophoresis or by anion-exchange HPLC as described in Pearson, J. D. and Regnier, F. E. (1983) *J. Chrom.* 255:137–149. The sequence of the synthetic oligonucleotide can be verified using the chemical degradation method of Maxam, A. M. and Gilbert, W. (1980) in *Methods Enzymol.* 65:499–560.

Typically, the probes used to detect hybridization are labeled to facilitate detection. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like. Other labels include ligands which bind to labeled antibodies, fluorophores, chemiluminescent agents, enzymes, and antibodies which can serve as specific binding pair members for a labeled ligand. (Tijssen, P., "Practice and Theory of Enzyme Immunoassays" in Burdon, R. H., van Knippenberg, P. H. (eds.) (1985) Laboratory Techniques in Biochemistry and Molecular Biology, Elsevier, pp. 9–20.)

One method for evaluating the presence or absence of particular nucleic acids in a sample involves a Southern transfer. Briefly, digested genomic DNA is run on agarose slab gels in buffer and transferred to membranes. Target nucleic acids are detected using labeled probes.

Similarly, a Northern transfer may be used for the detection of particular RNA molecules. In brief, total RNA is isolated from a given cell sample using an acid guanidiniumphenol-chloroform extraction method. The RNA is then electrophoresed to separate the RNA species and the RNA is transferred from the gel to a nitrocellulose membrane. As with the Southern blots, labeled probes are used to identify the presence or absence of particular RNAs.

An alternative means for determining the level of expression of a specific nucleic acid is in situ hybridization. In situ hybridization assays are well known and are generally described in Angerer, et al. (1987) *Methods Enzymol.* 152:649–660. In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to the targeted nucleic acids. The probes are preferably labeled with radioisotopes or fluorescent reporters.

The sensitivity of the hybridization assays may be enhanced through use of a nucleic acid amplification system which multiplies the target nucleic acid being detected. in vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Q-replicase amplification and other RNA polymerase mediated techniques (e.g., NASBA) are found in Berger, Sambrook, and Ausubel, as well as Mullis et al. (1987) U.S. Pat. No. 4,683,202; Innis et al. (eds.) (1990) *PCR Protocols A Guide to Methods and Applications*, Academic Press, Inc., San Diego, Calif. (Innis); Arnheim & Levinson (Oct. 1, 1990) C&EN 36–47; (1991) *J. NIH Res.* 3:81–94; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al. (1988) *Science* 241:1077–1080; Van Brunt (1990) *Biotechnology* 8:291–294; Wu and Wallace (1989) *Gene* 4:560; Barringer et al. (1990) *Gene* 89:117, and Sooknanan and Malek (1995) *Biotechnology* 13:563–564.

A preferred method of amplifying target sequences is the polymerase chain reaction (PCR). In PCR techniques, oligonucleotide primers complementary to the two 3' borders of the nucleic acid region to be amplified are synthesized. The polymerase chain reaction is then carried out using the two primers. See Innis, M., Gelfand, D., Sninsky, J. and White, T. (eds.) (1990) PCR Protocols: A Guide to Methods and Applications Academic Press, San Diego. Primers can be selected to amplify the entire regions encoding a full-length ribozyme or selected subsequence, or to amplify smaller nucleic acid segments as desired.

vii. Detection of Protein Gene Products

Gene products such as polypeptides may be detected or quantified by a variety of methods. Preferred methods involve the use of specific antibodies.

Methods of producing polyclonal and monoclonal antibodies are known to those of skill in the art. See, e.g., Coligan (1991) Current Protocols in Immunology Wiley/Greene, N.Y.; and Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; Goding (1986) Monoclonal Antibodies: Principles and Practice (2d ed.) Academic Press, New York, N.Y.; and Kohler and Milstein (1975) *Nature* 256:495–497. Such techniques include antibody preparation by selection of antibodies from libraries of recombinant antibodies in phage or similar vectors. See, Huse et al. (1989) *Science* 246:1275–1281; and Ward et al. (1989) *Nature* 341:544–546. For example, in order to produce antisera for use in an immunoassay, an immunogen polypeptide or a fragment thereof is isolated or obtained as described herein. Mice or rabbits, typically from an inbred strain, are immunized with the immunogen protein using a standard adjuvant, such as Freund's adjuvant, and a standard immunization protocol. Alternatively, a synthetic peptide derived from proteins disclosed herein and conjugated to a carrier protein can be used as an immunogen.

Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against protein related or unrelated to the immunogen, using a competitive binding immunoassay. Specific monoclonal and polyclonal antibodies and antisera will usually bind to the immunogen with a $K_D$ of at least about 0.1 mM, more usually at least about 1 micromolar, preferably at least about 0.1 micromolar or better, and most preferably 0.01 micromolar or better.

A number of immunogens may be used to produce antibodies specifically reactive with a particular peptide antigen. Recombinant protein is the preferred immunogen for the production of monoclonal or polyclonal antibodies. Naturally occurring protein may also be used either in pure or impure form. Synthetic peptides made using the sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the immunogen. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein (1976) *Eur. J. Immunol.* 6:511–519 incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate nucleic acid sequences which encode a monoclonal antibody or a binding fragment thereof by screening a DNA library from human B cells according to the general protocol outlined by Huse, et al. (1989) *Science* 246:1275–1281.

A particular protein can be measured by a variety of immunoassay methods. For a review of immunological and immunoassay procedures in general, see Basic and Clinical Immunology 7th Edition (D. Stites and A. Terr ed.) 1991. Moreover, the immunoassays of the present invention can be performed in any of several configurations, which are reviewed extensively in Maggio, E. T. (ed.) (1980) *Enzyme Immunoassay*, CRC Press, Boca Raton, Fla.; Tijssen, P. (1985) "Practice and Theory of Enzyme Immunoassays" in Laboratory Techniques in Biochemistry and Molecular Biology, Elsevier Science Publishers B.V. Amsterdam; and, Harlow and Lane, Antibodies, A Laboratory Manual, supra, each of which is incorporated herein by reference.

Immunoassays to peptides of the present invention may use a polyclonal antiserum which was raised to a defined protein, or a fragment thereof. This antiserum is selected to have low crossreactivity against other proteins and any such crossreactivity (for example, cross-reactivity against equivalent proteins from different species or tissues) is removed by immunoabsorbtion prior to use in the immunoassay.

In order to produce antisera for use in an immunoassay, the antigen protein, or a fragment thereof is isolated as described herein. For example, recombinant protein is produced in a transformed cell line. An inbred strain of mice such as balb/c is immunized with the selected protein of using a standard adjuvant, such as Freund's adjuvant, and a standard mouse immunization protocol. Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against proteins other than the antigen, using a competitive binding immunoassay such as the one described in Harlow and Lane, supra, at pages 570–573.

Immunoassays in the competitive binding format can be used for the crossreactivity determinations. For example, the selected protein can be immobilized to a solid support. Proteins (either distinct from, or related to, the antigenic protein) are added to the assay which compete with the binding of the antisera to the immobilized antigen. The ability of the above proteins to compete with the binding of the antisera to the immobilized protein is compared to the antigenic protein. The percent crossreactivity for the above proteins is calculated, using standard calculations. Those antisera with less than 10% crossreactivity with the antigenic proteins are selected and pooled. The cross-reacting antibodies are optionally removed from the pooled antisera by immunoabsorbtion with the above-listed proteins.

The immunoabsorbed and pooled antisera are then used in a competitive binding immunoassay as described above to compare a second protein to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the immunogen protein that is required, then the second protein is said to specifically bind to an antibody generated to the immunogen protein.

The presence of a desired polypeptide (including peptide, transcript, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to protein on the solid support. These antibodies are directly labeled, or alternatively are subsequently detected using labeling agents such as antibodies (e.g., labeled sheep anti-mouse antibodies where the antibody to a protein is a murine antibody) that specifically bind to the labeling antibody.

c. Isolation of Nucleic Acids

There are various methods of isolating nucleic acid sequences which encode ribozymes or other desired gene products. See Sambrook et al. For example, DNA is isolated from a genomic or cDNA library by hybridization to immobilized oligonucleotide probes complementary to the desired sequences. Alternatively, probes designed for use in amplification techniques such as PCR are used, and the desired nucleic acids may be isolated using methods such as PCR. In addition, nucleic acids having a defined sequence may be chemically synthesized in vitro. Finally, mixtures of nucleic acids may be electrophoresed on agarose gels, and individual bands excised.

Methods for making and screening cDNA and genomic DNA libraries are well known. See Gubler, U. and Hoffman, B. J. (1983) *Gene* 25:263–269 and Sambrook et al, supra. To prepare a genomic library, the DNA is generally extracted from cells and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al. The vector is transfected into a recombinant host for propagation, screening and cloning. Recombinant phage are analyzed by plaque hybridization as described in Benton and Davis (1977) *Science* 196:180–182. Colony hybridization is carried out as generally described in M. Grunstein et al. (1975) *Proc. Natl. Acad. Sci. USA*, 72:3961–3965.

A cDNA library is generated by reverse transcription of total cellular mRNA, followed by in vitro packaging and transduction into a recombinant host.

DNA encoding a particular gene product is identified in either cDNA or genomic libraries by its ability to hybridize with nucleic acid probes, for example on Southern blots, and these DNA regions are isolated by standard methods familiar to those of skill in the art. See Sambrook et al.

Once a desired nucleic acid is detected in a mixture of nucleic acids, it is ligated into an appropriate vector and introduced into an appropriate cell, and cell clones that contain only a particular nucleic acid are produced. Preferably, strains of bacterial cells such as *E. coli* are used for cloning, because of the ease of maintaining and selecting bacterial cells.

PCR can be also used in a variety of protocols to isolate nucleic acids. In these protocols, appropriate primers and probes for amplifying a nucleic acid encoding a particular sequence are generated from analysis of the nucleic acid sequences listed herein. Once such regions are PCR-amplified, they can be sequenced and oligonucleotide probes can be prepared from the sequence obtained. These probes can then be used to isolate nucleic acid's encoding the sequence.

Other methods known to those of skill in the art may also be used to isolate particular nucleic acids. See Sambrook, et al. for a description of other techniques for the isolation of nucleic acid encoding specific protein molecules. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

d. Isolation and Purification of Polypeptide Gene Products

The polypeptides of this invention may be purified to substantial purity by standard techniques, including selective precipitation with such substances as ammonium sulfate, column chromatography, immunopurification methods, and others. See, for instance, R. Scopes (1982) Protein Purification: Principles and Practice, Springer-Verlag: New York, incorporated herein by reference. For example, the proteins and polypeptides produced by recombinant DNA technology may be purified by a combination of cell lysis (e.g., sonication) and affinity chromatography or immunoprecipitation with a specific antibody to the target protein. For fusion products, subsequent digestion of the fusion protein with an appropriate proteolytic enzyme releases the desired polypeptide. The proteins may then be further purified by standard protein chemistry techniques.

e. Ribozyme Expression in Transgenic and Chimeric Animals

The ribozymes in the ribozyme library can be expressed in a chimeric animal or in a non-human transgenic animal. The transgenic animals of the invention comprise any non-human animal or mammal, such as non-human primates, ovine, canine, bovine, rat and murine species as well as rabbit and the like. Preferred non-human animals are selected from the rodent family, including rat, guinea pig and mouse, most preferably mouse.

Generally, a female non-human animal is induced to superovulate by the administration of hormones such as follicle-stimulating hormone, the eggs are either collected and fertilized in vitro or the superovulated female is mated to a male and the zygotes are collected, and the zygote is transduced with one or more selected vectors comprising a ribozyme library and/or a preselected nucleic acid. In the case of zygotes the preferred method of transgene introduction is by microinjection. However, other methods such as retroviral or adenoviral infection, electroporation, or liposomal fusion can be used.

Specific methods for making transgenic non-human animals are described in the following references: Pinkert C. A. (ed.) (1994) Transgenic Animal Technology: A Laboratory Handbook Academic Press and references cited therein; Pursel et al. (1989) Genetic engineering of livestock, Science 244:1281–1288, especially p. 1282–1283, Table 1 at p. 1283; Elbrecht A. et al. (1987) "Episomal Maintenance of a Bovine Papilloma Virus Vector in Transgenic Mice," Mol. Cell. Biol. 7(3):1276–1279; Hammer et al. (1985) "Production of transgenic rabbits, sheep and pigs by microinjection," Nature 315:680–683; Hughes et al. (1990) "Vectors and genes for the improvement of animal strains" J. Reprod. Fert., Suppl. 41:39–49; Inoue et al. (1989) "Stage-dependent expression of the chicken-crystallin gene in transgenic fish embryos," Cell Differen. Devel. 27:57–68; Massey, J. M. (1990) "Animal production industry in the year 2000 A.D.," J. Reprod. Fert., Suppl., 41:199–208; Rexroad, C., et al. (1989) "Production of Transgenic Sheep With Growth-Regulating Genes," Mol. Reprod. Devel. 1:164–169; Rexroad, C., et al. (1990), "Insertion, expression and physiology of growth-regulating genes in ruminants," J. Reprod. Fert., Suppl., 41:119–124; Simons et al. (1988) "Gene transfer into sheep," Bio/Technology, 6:179–183; Squire et al. (1989) "in vitro testing of a potential retroviral vector for producing transgenic livestock," Am. J. Vet. Res., 50(8) 1423–1427; Wall, R. J. (1989) "Use of transgenic animals in livestock improvement," Animal Genetics, 20:325–327; Ward et al. (1990) "The potential of transgenic animals for improved agricultural productivity," Rev. Sci. Tech. Off. Int. Epiz., 9(3):847–864; Westphal, H. (1989) "Transgenic mammals and biotechnology," The FASEB Journal, 3:117–120, all of which are incorporated by reference. There is even a Journal, "Transgenic Research", exclusively dedicated to this field.

In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. USA 82:4438–4442). As a consequence, all cells of the transgenic non-human animal will carry the incorporated transgene. This will, in general, also be reflected in the efficient transmission of the transgene to offspring of the founder since 50% of the germ cells will harbor the transgene.

The gene sequence being introduced need not be incorporated into any kind of self-replicating plasmid or virus (Jaenisch (1988) Science 240:1468–1474 (1988)). Indeed, the presence of vector DNA has been found, in some cases, to be undesirable (Hammer et al. (1987) Science 235:53; Chada et al. (1986) Nature 319:685; Kollias et al. (1986) Cell 46:89; Shani (1986) Molec. Cell. Biol. 6:2624 (1986); Chada et al. (1985) Nature, 314:377; Townes et al. (1985) EMBO J. 4:1715).

Once members of a ribozyme library, or any other DNA molecule are injected into the fertilized egg cell, the cell is implanted into the uterus of a receptive female (i.e., a female whose uterus is primed for implantation, either naturally or by the administration of hormones), and allowed to develop into an animal. Since all of the animal's cells are derived from the implanted fertilized egg, all of the cells of the resulting animal (including the germ line cells) shall contain the introduced gene sequence. If, as occurs in about 30% of events, the first cellular division occurs before the introduced gene sequence has integrated into the cell's genome, the resulting animal will be a chimeric animal.

By breeding and inbreeding such animals, it has been possible to produce heterozygous and homozygous transgenic animals. Despite any unpredictability in the formation of such transgenic animals, the animals have generally been found to be stable, and to be capable of producing offspring which retain and express the introduced gene sequence.

The success rate for producing transgenic animals is greatest in mice. Approximately 25% of fertilized mouse eggs into which DNA has been injected, and which have been implanted in a female, will become transgenic mice.

AAV or retroviral infection can also be used to introduce a transgene into an animal. Here, AAV are preferred because high m.o.i. infections can result in multiple copies stably integrated per cell. Multiple copies of transgene are beneficial because: (a) increased level of transgene expression, (b) it reduces the chance that the target cell will lose or "kick out" the transgene, (c) transgene expression is not completely lost if one copy is mutated or inactivated and (d) it increases the likelihood of transgene expression in all lineages when the original target cell undergo any differentiation. The developing non-human embryo can be cultured in vitro to the blastocyst stage. During this time, the blastomeres can be targets for retroviral infection (Jaenich (1976) Proc. Natl. Acad. Sci USA 73:1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner et al. (1985) Proc. Natl. Acad. Sci. USA 82:6927–6931; Van der Putten et al . (1985) Proc. Natl. Acad. Sci. USA 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the mid-gestation embryo (Jahner et al. (1982) supra).

A third and preferred target cell for transgene introduction is the embryonic stem cell (ES). ES cells are obtained from pre-implantation embryos cultured in vitro and fused with embryos (Evans et al. (1981 ) Nature 292:154–156; Bradley et al. (1984) Nature 309:255–258; Gossler et al. (1986) Proc. Natl. Acad. Sci USA 83:9065–9069; and Robertson et al. (1986) Nature 322:445–448). Transgenes can be efficiently introduced into the ES cells a number of means well known to those of skill in the art. Such transformed ES cells can thereafter be combined with blastocysts from a non-human animal. The ES cells thereafter colonize the embryo and contribute to the germ line of the resulting chimeric animal (for a review see Jaenisch (1988) Science 240:1468–1474).

The DNA molecule containing the desired gene sequence may be introduced into the pluripotent cell by any method which will permit the introduced molecule to undergo recombination at its regions of homology. Transgenes can be efficiently introduced into the ES cells by DNA transfection or by retrovirus-mediated transduction.

In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable (selectable) marker gene sequence.

In one embodiment, the presence of the detectable (selectable) marker sequence in a recipient cell is recognized by hybridization, by detection of radiolabelled nucleotides, or by other assays of detection which do not require the expression of the detectable marker sequence. In one embodiment, such sequences are detected using polymerase chain reaction (PCR) or other DNA amplification techniques to specifically amplify the DNA marker sequence (Mullis et al. (1986) Cold Spring Harbor Symp. Quant. Biol. 51:263–273; Erlich et al. EP 50,424; EP 84,796, EP 258,017 and EP 237,362; Mullis EP 201,184; Mullis et al., U.S. Pat. No. 4,683,202; Erlich U.S. Pat. No. 4,582,788; and Saiki et al. U.S. Pat. No. 4,683,194).

Most preferably, however, the detectable marker gene sequence will be expressed in the recipient cell, and will result in a selectable or at least a detectable phenotype. Selectable markers are well known to those of skill in the art. Some examples include the hprt gene (Littlefield (1964) Science 145:709–710), the tk (thymidine kinase) gene of herpes simplex virus (Giphart-Gassler et al. (1989) Mutat, Res. 214:223–232), the nDtll gene (Thomas et al. (1987) Cell 51:503–512; Mansour et al. (1988) Nature 336:348–352), or other genes which confer resistance to amino acid or nucleoside analogues, or antibiotics, etc.

Thus, for example, embryonic cells which express an active HPRT enzyme are unable to grow in the presence of certain nucleoside analogues (such as 6-thioguanine, 8-azapurine, etc.), but are able to grow in media supplemented with HAT (hypoxanthine, aminopterin, and thymidine). Conversely, cells which fail to express an active HPRT enzyme are unable to grow in media containing HATG, but are resistant to analogues such as 6-thioguanine, etc. (Littlefield (1964) Science 145:709–710). Cells expressing active thymidine kinase are able to grow in media containing HAT, but are unable to grow in media containing nucleoside analogues such as bromo-deoxyuridine (Giphart-Gassler et al. (1989) Mutat. Res. 214:223–232). Cells containing an active HSV-tk gene are incapable of growing in the presence of gangcylovir or similar agents. This strategy can be useful following gene delivery to either ES cells or unfertilized eggs. The HSV-tk approach is especially suited to ES/blastocyst delivery or selelction of developing zygotes since the "bystander effect" of tk (Freeman et al. (1996) Seminars in Oncology 23:31; Chen et al. (1995) Human Gene Therapy 6:1467) will kill not only the transduced cells but also the surrounding non-transduced cells. If genes are delivered to an unfertilized egg, both selection strategies can be applied, most suitably once fertilization has occurred and the cells begin to divide.

The detectable marker gene may also be any gene which can compensate for a recognizable cellular deficiency. Thus, for example, the gene for HPRT could be used as the detectable marker gene sequence when employing cells lacking HPRT activity. Thus, this agent is an example of agents may be used to select mutant cells, or to "negatively select" for cells which have regained normal function.

Chimeric or transgenic animal cells of the present invention are prepared by introducing one or more DNA molecules into a precursor pluripotent cell, most preferably an ES cell, or equivalent (Robertson in Capecchi, M. R. (ed.) (1989) Current Communications in Molecular Biology, Cold Spring Harbor Press, Cold Spring Harbor, N.Y., pp. 39–44). The term "precursor" is intended to denote only that the pluripotent cell is a precursor to the desired ("transfected") pluripotent cell which is prepared in accordance with the teachings of the present invention. The pluripotent (precursor or transfected) cell may be cultured in vivo, in a manner known in the art (Evans et al. (1981) Nature 292:154–156) to form a chimeric or transgenic animal. The transfected cell, and the cells of the embryo that it forms upon introduction into the uterus of a female are herein referred to respectively, as "embryonic stage" ancestors of the cells and animals of the present invention.

Any ES cell may be used in accordance with the present invention. It is, however, preferred to use primary isolates of ES cells. Such isolates may be obtained directly from embryos such as the CCE cell line disclosed by Robertson, E. J., In Capecchi, M. R. (ed.) (1989) Current Communications in Molecular Biology, Cold Spring Harbor Press, Cold Spring Harbor, N.Y., pp. 39–44), or from the clonal isolation of ES cells from the CCE cell line (Schwartzberg et al. (1989) Science 212:799–803). Such clonal isolation may be accomplished according to the method of Robertson in Robertson, E. J. (ed.) (1987) Teratocarcinomas and Embryonic Stem Cells: A Practical Approach, IRL Press, Oxford. The purpose of such clonal propagation is to obtain ES cells which have a greater efficiency for differentiating into an animal. Clonally selected ES cells are approximately 10-fold more effective in producing transgenic animals than the progenitor cell line CCE. An example of ES cell lines which have been clonally derived from embryos are the ES cell lines, AB1 (hprt$^+$) or AB2.1 (hprt$^-$).

In a preferred embodiment this invention utilizes Ola-derived E14 ES cells. The E14 embryonic stem cells are in the American Type Tissue Culture Repository at 12301 Parklawn Dr., Rockville, Md. USA, under accession number CRL1821.

The ES cells are preferably cultured on stromal cells (such as STO cells (especially SNL76/7 STO cells) and/or primary embryonic G418 R fibroblast cells) as described by Robertson, supra. Methods for the production and analysis of chimeric mice are well known to those of skill in the art (see, for example, Bradley in Robertson, E. J. (ed.) (1987) Teratocarcinomas and Embryonic Stem Cells; A Practical Approach, IRL Press, Oxford, pp. 113–151). The stromal (and/or fibroblast) cells serve to eliminate the clonal overgrowth of abnormal ES cells. Preferably, the cells are cultured in the presence of leukocyte inhibitory factor ("lif") (Gough et al. (1989) Reprod. Fertil. 1:281–288; Yamamori et al. (1989) Science 246:1412–1416).

ES cell lines may be derived or isolated from any species (for example, chicken, etc.), although cells derived or isolated from mammals such as rodents, rabbits, sheep, goats, fish, pigs, cattle, primates and humans are preferred. Cells derived from rodents (i.e. mouse, rat, hamster etc.) are particularly preferred.

f. How to Distinguish Between Ribozyme Effects Due Only to Binding to the Target RNA as Opposed to Cleaving the RNA Distinguishing between true catalytic activity and antisense activity is critical for the selection of active ribozymes. Assays in cell culture allow selection of specific ribozymes out of the AAV-delivered ribozyme library. Ribozymes initially selected inactivate expression of the target through either truly catalytic or simply antisense mechanisms. Less likely, although possible, the integration of the AAV genome could disrupt gene function as well.

To confirm that an observed phenotype is ribozyme dependent (and not due to AAV integration or to a spontaneous incidental mutation elsewhere in the genome), the AAV-ribozyme genome is "rescued" from the host cell genome by transfection with a plasmid expressing the AAV viral proteins along with infection with wild type adenovirus. The AAV produced from these transfected/infected cells rescue and package the original AAV-ribozyme genome into new AAV particles. These are then used to infect fresh cells and assayed for loss of gene function. Ribozyme-dependent activity would continue to knock out the specific gene.

To verify that the ribozyme-dependent activity is due to catalytic rather than simply antisense, the selected ribozyme gene is structurally modified to abolish the cleavage activity without affecting substrate binding. This is also important so that a unique probe to the gene, including the GUC, can be generated. A three base mutation of AAA to CGU in loop 2 of the hairpin ribozyme (FIG. 1) has been identified that disables the ribozyme cleavage activity without disrupting its substrate binding (Anderson et al. (1994) Nucleic Acids Res. 22:1096; Ojwang et al. (1992) Proc. Natl. Acad. Sci. USA 89:10802). This mutation is then introduced into the selected ribozymes by PCR amplification using the 3' disabled primer that contains the mutation. This new pool of "disabled" selected ribozymes is then re-introduced into AAV and assayed again for activity in cell culture. All AAV-disabled ribozyme clones that retain the ability to inactivate gene expression function through an antisense mechanism, while AAV-disabled ribozyme clones that lose this ability are indicative of an activity dependent on the ribozymes catalytic activity.

g. Uses of Ribozyme Gene Vector Libraries

Hairpin ribozyme libraries with randomized ribozyme recognition sites are used in a variety of Ribozyme-Mediated Gene Functional Analyses (RiMGFA), in which comparison of biological properties of cells with or without gene-inactivating ribozymes reveals the function and/or identity of a given gene.

The methods described herein are used to detect and then isolate unknown genes that result in a measurable phenotypic traits. A ribozyme that is shown to result in a given phenotype is isolated and sequenced. The ribozyme recognition sequence is used to detect, isolate and characterize genes that contain sequences complementary to the recognition sequence. For example, the methods of the invention are used to detect genes that mediate sensitivity and resistance to a selected defined chemical substance; examples include: drug toxicity genes; genes that encode resistance or sensitivity to carcinogenic chemicals; genes that encode resistance or sensitivity to infections with specific viral and bacterial pathogens. The methods of the invention are also used to detect unknown genes that mediate binding to a ligand, such as hormone receptors, viral receptors, and cell surface markers. The methods of the invention are also used to detect unknown tumor suppressor, transformation, and differentiation genes.

The simplest application of RiMGFA is the generation of target specific libraries. Most RNA targets (viral RNA, cellular mRNA, etc.) are relatively large (i.e. >1 kb) and the sequence is not always known, especially if the target RNA is generated from genomic DNA fragments deduced by population genetics and restriction fragment length polymorphisms (RFLPs). In addition, we have found secondary structure within certain RNA targets to be a serious hindrance to ribozyme cleavage (Welch et al. (1996) Gene Therapy 3:994). Historically, functional ribozyme cleavage sites have been deduced by brute force, synthesizing individual ribozymes one at a time and assaying their activity on a large target RNA in vitro. Furthermore, in many instances, ribozymes that cleave in vitro do not cleave in vivo (Welch et al. (1996) Gene Therapy 3:994). One goal of this technology is to start with a "library" of ribozymes, containing all possible target recognition sequences and select and enrich for specific ribozymes most active at inactivating the expression of a specific gene or ablating a specific gene function in vivo.

The particular phenotype and the method of measuring it vary with the kind of gene under examination. The effects of ribozymes on nucleic acids that encode receptors (e.g., hormone or drug receptors, such as platelet-derived growth factor receptor ("PDGFr") is measured in terms of differences of binding properties, differentiation, or growth. Effects on transcription regulatory factors are measured in terms of the effect of ribozymes of transcription levels of affected genes. Effects on kinases are measured as changes in levels and patterns of phosphorylation. Effects on tumor suppressors and oncogenes are measured as alterations in transformation, tumorigenicity, morphology, invasiveness, adhesiveness and/or growth patterns. The list of type of gene function and phenotype that is subject to alteration goes on: viral susceptibility—HIV infection; autoimmunity—inactivation of lymphocytes; drug sensitivity—drug toxicity and efficacy; graft rejection—MHC antigen presentation, etc.

h. In Vitro Identification of Efficient Site-specific Ribozymes from a Random Ribozyme Library and the Generation of Target Specific Libraries Some applications contemplate the in vitro identification of efficient site-specific ribozymes prior to their in vivo expression. Additionally, when the target RNA is large, it may be desirable to create a library of ribozymes each with specificity for different sites within the same target (a "target-specific" library). While these can be accomplished by a number of known methods, two preferred methods are further described. The first takes advantage of the inherent ability of the hairpin ribozyme to catalyze a trans-ligation reaction between the products of the cleavage reaction. By creating a self-cleavable ribozyme library, the trans-ligation reaction will join the specific ribozyme to one of its cleavage products. The ligated ribozymes now can be selectively amplified out of the library. The second preferred method is to immobilize the target RNA on a solid support, thus allowing soluble ribozymes to be selected based on their ability to bind, cleave and elute off of the target. The target can be any RNA (e.g. cellular or viral RNA), or DNA that has been converted to RNA. It is preferable to immobilize the target RNA by its 5' end (see below), but RNA immobilized via its 3' end is also suitable. Since both of these methods will positively select and amplify only actively cleaving ribozymes, they are far superior to previously published and patented methods such as brute force cloning of individual ribozymes (Welch et al. (1996) Gene Therapy 3:994) or the construction of "quasi-random" ribozymes (Draper et al. (1996) U.S. Pat. No. 5,496,698). These considerations become especially important if the target RNA is large (e.g. hepatitis C virus RNA~9.5 kb) and/or has an unknown sequence (e.g. large chromosomal DNA fragments converted to RNA).

i. Trans-ligation of Specific Ribozymes to Their Cleavage Products

The hairpin ribozyme is capable of cleaving a target RNA in both a cis and trans configuration (Bruening et al (1988) Structure and Expression, Vol. 1, p.239–248; Hampel et al (1988) Biochemistry 28:4929). It also has the ability to readily catalyze the reverse of the cleavage reaction and religate the cleavage products to reform the original substrate RNA (Hegg et al (1995) Biochemistry 34:15813; Joseph et al (1993) Genes and Development 7:130) In fact, in the presence of an excess of cleavage products the ligation reaction is favored over that of the cleavage reaction by a factor of ten (Hegg et al (1995) Biochemistry 34:15813).

This ligation reaction can be applied in the generation of target specific libraries. An elegant and efficient method for accomplishing this task is to make use of the ribozyme as a molecular tag. This ribozyme tag will provide a universal upstream primer for the subsequent isolation and amplification of the reaction products. This will facilitate the identification and sequence determination of the unique cleavage sites present within the target RNA and be used to generate a target specific ribozyme gene vector library.

To utilize the ribozyme as a molecular tag, the ribozyme must be capable of catalyzing trans-ligation at the site of cleavage within the target RNA. This can be accomplished by designing a combinatorial ribozyme library that first undergoes an autolytic cleavage. This self-processed library is then incubated in a trans-cleavage reaction with the target RNA of interest and, with a certain frequency, the ribozyme will become covalently attached to the target RNA at the site if cleavage through trans-ligation (FIG. 10). Specifically, a ribozyme combinatorial library will be constructed wherein the inter-molecular helices I and II will be completely randomized. This library will also contain, attached to its 3' end, a completely randomized cis-cleavage site having only a 3 bp helix I and helix II. The cis-cleavage site is tethered to the 3' end of the ribozyme by means of a 5 bp polypyrimidine tract. The ribozyme library is transcribed and concurrently will undergo the cis-cleavage reaction. This will generate a pool of randomized ribozymes also having a randomized helix II cleavage product still attached to the ribozyme. The presence if this helix II cleavage product is important for two reasons. The first being, as a localized source of readily available helix II cleavage products suitable for ligation and the second, is the fact that the helix II cleavage product contains the 2'3' cyclic phosphate necessary for providing the energy required to drive the ligation reaction. This pool of 'helix II charged ribozymes' is then purified from the rest of the library and used in a trans-cleavage reaction with the target RNA under standard cleavage conditions. The ribozyme will cleave the target at specific sites and, with a certain frequency, the ribozyme will become covalently attached to the target RNA at these sites by means of the trans-ligation reaction (FIG. 10).

The identification of these unique cleavage sites is then determined by RT-PCR. The reaction products from the trans-cleavage reaction are reacted with polyA-polymerase to generate a polyA tail on the 3' end of the reaction products. The RNA is then reverse transcribed using oligo-dT as the primer. This resulting cDNA is then amplified by PCR using the oligo dT as the downstream primer and a universal upstream primer provided by the ligated ribozyme sequence. The reaction products are amplified by PCR and can be sequenced directly or after subcloning. To generate a target specific ribozyme gene vector library, the selected ribozyme genes are further cloned into AAV vectors.

ii. Immobilizing Target RNA Via its 5' End

If the target RNA has a 5' methyl-G cap (such as cellular mRNA and many viral RNAs), the RNA can be immunoprecipitated using monoclonal antibodies directed against the cap structure (Garcin and Kolakofsky, 1990; Weber, 1996) and immobilized on Protein G sepharose beads (Pharmacia, Uppsala, Sweden) (see FIG. 7). If the target RNA is not capped (such as some viral RNAs, non-messenger cellular RNA or RNA transcribed in vitro), it can be bound to streptavidin-agarose beads (Pierce, Rockford Ill.) via a 30-mer oligonucleotide that is biotinylated at its 3' end (see FIG. 7). The sequence of the 30-mer is complementary to the 5' end of the target RNA. If the target is a known viral or cellular RNA, the oligo is designed based on the known sequence of the RNA's 5' end. If the target RNA comes from genomic DNA of unknown sequence that has been converted to RNA via retrovirus packaging, the oligo is designed based on the retroviral-specific immediate 5' sequence transcribed from the LTR. Likewise DNA cloned into in vitro transcription vectors and transcribed by T7 RNA polymerase to yield the target, are engineered to contain specific 30 nt at their 5' end, upstream of the actual target sequence. In general, then, the 3' end of the specific 30-mer biotinylated oligo is bound to the streptavidin column and the 5'30 nt bind the target RNA by Watson-Crick base pairing (see FIG. 7). To prepare the column, the biotinylated oligo is incubated with the beads and unbound oligo is washed out. The target RNA is then mixed with the oligo column, heated to 95° C. and cooled slowly to allow annealing of the oligo and target RNA. The column is then washed to remove unbound target RNA.

iii. Immobilizing Target RNA Via its 3' End

It is occasionally necessary to immobilize the target RNA by its 3' end. If the target RNA is polyadenylated mRNA, a simple oligo d(T)$_{30}$ column would bind the target RNA (Pharmacia) (FIG. 7). If the target RNA is not polyadenylated (or if one wishes a stronger binding than simple Watson-Crick basepairing), the 3' end of the RNA can be biotinylated using biotin-UTP (Sigma, St. Louis, Mo.) and terminal transferase (Promega, Madison, Wis.), according to the manufacturers. The biotinylated target can then be immobilized on streptavidin-agarose beads (Pierce, Rockford Ill.) (FIG. 7).

iv. Ribozyme Library Preparation

This application involves the use of a library of randomized ribozymes as opposed to randomized ribozyme genes. in vitro synthesis of the ribozymes encoded by the library is accomplished by transcribing the double-stranded ribozyme gene library (described in Specific Example a.) with T7 RNA polymerase, as described (Welch, P. J., et al. (1996) Gene Therapy 3:994–1001). For later tracking and selection purposes, the ribozyme library can be transcribed in the presence of trace amounts of P-32 UTP. The ribozyme library transcription reaction is then treated with DNase to remove the DNA template. Lastly, transcribed ribozymes are purified by polyacrylamide gel to enrich for full length transcripts. If desired, the ribozymes can be radio-labeled with [$^{32}$P]UTP, which can be used as a marker to follow the binding of the ribozymes at various stages of selection (see below).

v. Ribozyme Library Selection

The RNA target column is pre-treated with non-specific RNA (such as E. Coli rRNA or yeast tRNA), the ribozymes are loaded in the absence of magnesium, and the unbound non-specific RNA washed from the column (FIG. 8). This reduces non-specific binding of ribozyme to the column. The ribozyme library is then added to the RNA target column along with non-specific RNA, again in the absence of magnesium, thus allowing ribozyme binding without actual cleavage of the target RNA (Ojwang et al. (1992) Proc. Natl. Acad. Sci. USA 89:10802). For tracking and selection purposes, the ribozyme library can be transcribed in the presence of trace amounts of P-32 UTP, thus allowing quantitation of ribozyme binding and release throughout all the selection steps. The ribozyme library is added such that the target RNA is in molar excess, otherwise more than one ribozyme will be released from the column following a successful cleavage, generating false-positive results. The column is then washed free of unbound ribozyme. Specific ribozyme binding can be monitored by following the radioactivity remaining bound to the column. Magnesium-containing ribozyme cleavage buffer is then added to the column and the slurry is incubated at 37° C. for two hours to allow for substrate cleavage to occur. When a ribozyme successfully cleaves the target, it temporarily acts as a "bridge" between the 5' and 3' substrate products. Since the 5' product is bound by only a 4 bp helix, this interaction rapidly melts at 37° C. and the ribozyme is released from the solid support (FIG. 8). If the target RNA is immobilized via its 3' end, the cleaving ribozyme remains bound by the 7 bp helix, which will also rapidly melt at 37° C. (max T$_m$~22° C). Therefore, all "released" ribozymes are ones with activity against the target. These are then eluted and precipitated for amplification. Again, the specificity of the binding and cleavage reactions can be monitored by following the radioactivity present in the transcribed ribozymes. For proof that the selection procedure is successful, the initial library can be "spiked" with a known amount of purified ribozyme with known activity against the target (if available).

vi. PCR Amplification of Selected Ribozymes

Reverse transcriptase is used to convert the selected ribozyme pool to DNA using a primer specific to the 3' end of all the ribozymes (3' Primer). This primer includes the MluI site and a portion of the common region of the ribozyme and is therefore present in all ribozymes which were made in the library. The reverse transcriptase products are then amplified by standard PCR using a primer specific for the 5' end of all ribozymes in the library including a BamHI restriction site (5' Primer). This 5' primer used in this amplification step may or may not also include (at its 5' end) a T7 promoter arm for a future transcription steps. The PCR products are then purified and transcribed with T7 RNA polymerase. The resulting "selected" ribozymes are gel purified, and then used for a second (third, fourth, etc.) round of further selection on a fresh target column, bound, allowed to cleave and subsequently eluted and amplified as above until only specific, active ribozymes remain in the pool. Ribozyme binding and activity is continually monitored by following the location of the radiolabeled pool of ribozymes, and this is also used as a measure of specificity of the selection. For example, with an unselected pool of ribozyme the majority of the radiolabel will not even bind the column. Conversely, with a highly selected pool, most of the radiolabel would initially bind the column and then most would be released once magnesium was added. To avoid loss due to radioautolysis, ribozyme transcription, binding and selection is performed in one day. The subsequent PCR amplification products do not contain any radioactive nucleotides, and are therefore stable for long periods of time. Together, the combination of high-specificity binding and subsequent PCR amplification allows for conditions that are both selective and of high yield.

vii. Ribozyme Cloning, Sequencing, Identification of Sites and Target Gene Cloning Once satisfied with the selected pool of ribozymes, each specific ribozyme is cloned from its amplified double-stranded DNA template into a sequencing vector (e.g., pGem7Z, Promega) via the BamHI and MluI sites. Each ribozyme clone is then sequenced and the resulting sequence of the ribozyme binding arms is used to identify the site within the target (if the target sequence is known) or to generate a. DNA probe to clone the target gene (if the gene is unknown). To construct such a probe, the sequence of the ribozyme binding arms is combined with the requisite GUC to construct a DNA probe 5' XXXXXXXNGUCXXXX3' (where X is the deduced sequence coming from the specific ribozyme), which is then used to screen cDNA libraries to clone the gene.

viii. Selection Enhancement

If multiple rounds of selection on the same column still yield false positives due to release of inactive ribozymes bound downstream of an active one, the selected ribozymes are then applied to another column prepared with the RNA target bound to the column in the reverse orientation (i.e. if target bound on 5' previously, then switch to 3' immobilization). This re-screening and amplification is repeated as many times as necessary to satisfy pre-determined requirements set for the ribozymes to be selected (i.e. diversity of ribozyme number, ribozyme efficiency, total ribozyme number, etc.) If P-32 UTP is included in the ribozyme transcripts, as mentioned previously, the binding ratio of those ribozymes which remain bound to the target RNA on the column relative to that which has cleaved the target RNA can be tracked from screening to screening. Again, as selection progresses, this ratio will steadily shift greater for ribozymes which cleave the target RNA instead of remaining bound to the target. Furthermore, screening success can be quantified by the number of PCR cycles required to amplify the selected ribozymes (Conrad et al. (1995) *Molecular Diversity* 1:69). As the ribozyme pool is further selected and amplified, the number of required PCR cycles would be expected to reduce proportionally.

ix. Assembling Target-specific Ribozyme Gene Vector Libraries

Once the target-specific ribozymes have been selected, amplified and identified, the ribozyme genes are cloned into AAV vectors, resulting in a specific ribozyme gene vector library (see previous and later sections for cloning and application). The ribozyme fragment generated after PCR amplification contains BamHI and MluI restriction sites (see 5' Primer and 3' Primer). Digestion with the two enzymes not only generates cohesive ends for easy cloning into AAV vectors but also removes the T7 polymerase promoter sequences. Once generated, this library of AAV-ribozyme can be used for a variety of applications including, but not limited to, therapeutic and gene functional analysis in vivo.

i. Differential Ribozyme Gene Libraries

Frequently, when analyzing different cell types, it is necessary to determine how gene expression differs between the two cell types. For example, when attempting to determine the cause of tumor formation, one often wishes to compare gene expression between a transformed cell and its parental cell type. Other examples include cells before and after viral infection, or following a cell through various stages of differentiation. Previous methods for isolating such differentially-expressed genes (briefly described below) are time consuming, technically challenging and often yield many false positive results. Immusol's ribozyme library technology not only removes these disadvantages, but also results in a functional ribozyme or ribozymes that can immediately be used to knockout the gene or genes in question, for functional analysis.

Historically, a procedure called "subtractive hybridization" would be employed to determine which genes are differentially expressed (for review Ausubel, F., et al. (ed.) (1987) Current Protocols in Molecular Biology, Greene Publishing and Wiley-Interscience, New York. Briefly, mRNA or cDNA from each cell type are mixed and allowed to hybridize. The hybridized products (dsRNA or dsDNA) are then removed by column chromatography and the remaining, unhybridized nucleic acids (the differentially-expressed genes) are cloned. The main disadvantages, among others, of this method lies in its technical difficulty and its time consuming procedures.

More recently, a method called "differential display" has been developed (for review see Ausubel, F., et al. (ed.) (1987) Current Protocols in Molecular Biology, Greene Publishing and Wiley-Interscience, New York. Briefly, partially random primers are used in PCR to amplify a subset of mRNAs expressed in each cell type. The PCR products are then separated by polyacrylamide gel electrophoresis and the amplified bands between the two cell types are compared. Unique bands are excised from the gel, re-amplified and cloned. The main disadvantages of this method are that each PCR reaction only targets a subset of differentially-expressed genes. Indeed, many different primer sets (and subsequent PCR reactions) are required for a full representation of all mRNA species. In addition to generating many false-positives, differential display is really only suitable for detecting medium-to high-abundance mRNAs.

In one embodiment, the randomized ribozyme library of the present invention is used in vitro to both identify differentially-expressed genes and to generate specific, active ribozymes against the unique mRNAs. To accomplish this, mRNA is isolated from the two different cell lines in question (cell A and cell B). Individual target RNA columns are prepared for each cell type by either: a) binding the mRNAs by their 5' ends using a monoclonal antibody directed against the 5' methyl-G cap (for detailed discussion see above section on identification of ribozymes that cleave a known target RNA), bound to protein G-sepharose or b) binding the mRNAs by their 3' polyadenylated tails to an oligo(dT) column (again, see detailed discussion in identification of ribozymes that cleave a known target RNA). The ribozyme library is synthesized by in vitro transcription and applied to the column prepared from the mRNA of cell A under conditions that inhibit cleavage such as the absence of magnesium or low temperature (thus allowing ribozyme binding but not cleavage). Ribozymes that flow through this column represent targets not present in the mRNA pool of cell A. The bound ribozymes are then allowed to cleave by changing the conditions to favor cleavage (i.e. add magnesium or increase temperature). Active, specific ribozymes are then released from the solid support. Ribozymes that are released at this step are ones capable of both binding and cleaving RNA from cell A. These ribozymes are then applied to the RNA column from cell B under conditions that prevent cleavage. These cell A-specific ribozymes that also bind the cell B column represent ribozymes that recognize RNA targets present in both cells, while the ribozymes that flowthru are ones that recognize RNA only expressed in cell A. These ribozymes are then amplified, cloned and sequenced to produce a probe to clone the differentially-expressed, cell A-specific genes. Additionally, the specific ribozymes are cloned into AAV vectors which can be applied to cell A to analyze the effects and function of the differentially-expressed genes. Naturally, the above described process can be reversed (i.e. apply ribozymes to column B first then column A) to isolate genes differentially expressed in cell B.

Additionally, more than one differential selection method can be employed. For example, differential display could be used to generate RNA fragments specific for one cell type, and these RNA's could then be used to generate a target specific library.

j. Generation of and Transduction with a Ribozyme Gene Vector Library Pre-selected to Eliminate Lethal Ribozymes Transduction with the full ribozyme gene library can result in the expression of ribozymes directed against essential cellular genes. Cells expressing such "toxic" ribozymes will die. This is an especially important consideration when more than one ribozyme is delivered per cell, since the presence of a "toxic" ribozyme would automatically select out any other ribozyme genes in that same cell. In order to minimize the toxicity of the full library, the full library is transduced into the host cells, preferably at an m.o.i. of less than 1, and the ribozyme genes of surviving cells are rescued. The new library of rescued ribozyme genes encodes ribozymes that are not fatal to the host cell. This new library can be used to transduce host cells to detect in vivo ribozyme effects, or it can be used to screen for active ribozymes in vitro as described above. Additionally, this "pre-selection" is a particularly important screening step when it is necessary to introduce multiple ribozyme genes into one cell.

3. Specific Examples a. Synthesis of Ribozyme Gene Library with a Randomized Recognition Sequence Ribozyme genes with randomized recognition sequences were synthesized as follows: A 5' Primer (containing the T7 promoter, a BamHI restriction enzyme site and a region complementary to a 3' Synth Primer) was annealed to a 3' Synth Primer (which consists of an MIu I restriction enzyme site, the catalytic region of the ribozyme, the randomized binding arms and a region complementary to the 5' Primer) and the single-stranded regions were converted to double-stranded DNA. The nucleic acids comprising randomized ribozyme binding arms recognize the following target sequences: $(N)_4N^*GUC(N)_{6-10}$ or $(N)_4N^*GUA(N)_{6-10}$ (* denotes the cleavage site, and N can be any nucleotide). These oligonucleotides were synthesized in vitro by Retrogen (San Diego, Calif.). After synthesis, the oligonucleotides were purified as described previously. (Welch, P. J. et al. (1996) *Gene Therapy* 3:994–1001).

To create a clonable, double-stranded DNA containing the complete ribozyme gene sequence, the specific ribozyme oligonucleotide (3' synth primer, 1–2 g) was hybridized to the corresponding oligonucleotide (5' primer, 2–5 µg) and the single-stranded regions were converted to double-stranded DNA using Klenow DNA polymerase (Promega, Madison, Wis., USA). The completed double strand ribozyme library was amplified by PCR to increase the copy numbers of each ribozyme representative using purified 5' Primer and 3' Primer.

The amplified ribozyme gene library was transcribed in vitro to test the ribozyme library complexity by T7 polymerase (20–40 Units) as described in Welch, P. J. et al., (1996) *Gene Therapy* 3:994–1001).

The ribozyme library complexity was tested by cleaving known ribozyme target sites [found in HIV and HCV RNA sequences] (FIG. 2). The final library comprised about ~4×10⁶ individual species.

b. Insertion of the Library of Ribozyme Genes into an AAV Pro-vector

For cloning purposes, the specific ribozyme library oligonucleotides contain an MIuI restriction site, and the corresponding oligonucleotide contain BamHI restriction enzyme site. In order to optimize the efficiency of in inserting the ribozyme genes into the AAV cassette (and thus achieve maximal sequence complexity), two different approaches were used. In the first approach, a ribozyme gene library was generated by PCR and then subcloned and ligated into the AAV vector cassette. However, since ligation may be inefficient and may also result in incorporation of multiple inserts, a second approach for engineering the AAV random ribozyme vector library was to incorporate the ribozyme gene library into the vector directly by using "PCR cloning."

i. Approach 1

The vector pAMFT.dBam (FIG. 3)(modified from psub201 (Samulski R. J. 1987. J. Virol. 61: 3096–3101), was used in the first approach for ribozyme library gene cloning. pAMFT.dBam is a recombinant plasmid carrying 1) 5' and 3' inverted terminal repeats (ITR) of adeno-associated viral genome; 2) cassette for transcription and translation of gene of interests; 3) neomycin resistance marker pAMFT dBam (50 µg, 8129 bp) was thoroughly digested overnight at 37° C. with restriction enzymes BamHI and MIuI (200 Units each). The digestion reaction were terminated (and purified by phenol-chloroform extraction and the desired gene fragments isolated from agarose gel after gel electrophoresis. The in vitro synthesized ribozyme genes were also digested with BamHI and MIuI, and inserted to BamHI and MIuI restricted pAMFT dBam by ligation (200 Units of ligase) at 15° C. overnight. To increase the ligation efficiency of ribozyme gene insert into vector, several precautions were taken. 1) forced cloning (BamHI and MIuI restriction enzyme site flanked the insert); 2) no phosphatase (CIP) treatment for vector; 3) the restriction enzymes used were screened for absence of restriction exo- or endo-nuclease activity for best ends generation; 4) ligations were performed at various insert/vector rations. Efficiency of ligation were determined by counting numbers of transformed bacterial colonies formed after transforming with various amount of ligated DNA e.g. 1 µg, 2 µg, 5 µg, 10 µg, 50 µg and 100 µg. Table 1 shows the efficiency of ligation/transformation, indicating that 1 µg of ligated DNA can yield 4×10⁵ transformed colonies.

Recombinant AAV (rAAV) are produced by transient transfection of cells at 90% confluency in flat stock. pAAV/Ad helper plasmids that provide rep and cap proteins in trans were a kind gift of J. Samulski. The AAV ribozyme library pro-vector plasmids (pAMFT.dBam-ribozyme lib) are cotransfected with the pAAV/Ad helper at a ratio 1:1 using LipofectAmine (Life Technologies Inc.). Since low efficiency of co-transfection can account for low AAV titer, transfection of Hela cells with LipofectAmine were optimized (Table 2). Hela cells were transfected with 3 forms of DNA, 1) linear 2) closed after self ligation and 3) supercoil DNA induced by topoisomerase. The cells are infected with adenovirus type 5 (Ad5) at an MOI of 5–10 and harvested on day 4. Cells are lysed by nebulization and clarified by hollow fiber microfiltration followed by a concentration step using ultrafiltration. Clarified lysate is purified using a dual column chromatography process. The action exchange resin HS (Perseptives, Inc.) removes the majority of the contaminating proteins and DNA, the rAAV peak is eluted of in phosphate buffer pH 7.2, 300 mM NaCl, and immediately loaded on the anion exchange resin HQ (Perseptives, Inc.) where the adenoviral contamination is removed. The flow through is collected and heat inactivated at 56° C. for 2 hours to ensure the inactivation of any residual adenoviral contamination. The purified rAAV is formulated for storage.

The final product is tested for infectious titer, particle titer, residual DNA and protein, adenoviral contamination, and wild type AAV. Purified product from packaging cells is compared for quality and consistency in each test. Particle titer is determined by a slot blot procedure using radiolabelled probe and quantitated using a plasmid standard curve and previously titered vector. (Samulski et al. (1989) *J. Virol.* 63:3822.) Adenoviral contamination is determined by plaque assay (Graham and Van Der Eb (1973) *Virology* 42:456–467) following three amplification cycles on permissive cells. This assay is sensitive to ten infectious particles per milliliter. Wild type AAV is tested by QC-PCR analysis following three amplification cycles in the presence of adenovirus on permissive cells. This assay is sensitive to ten infectious particles per milliliter.

Dilutions of the heat inactivated rAAV lysate are added to 1×10⁵ HeLa cells/well plated in 6 well dishes. Titers of AAV-ribozyme-Lib preparations are determined by resistance to G418 as neo titer. High-titer (1×10⁹ particles/ml) preparations are stored at 80° C. until use.

ii. Approach 2. Construction of Full Length AAV Random Ribozyme Library Pro-vector by Using "PCR Cloning".

Since ligation may be inefficient and may result in the incorporation of multiple inserts, a second approach for generating the AAV random ribozyme vector library is to incorporate the random ribozyme gene library into the pAMFT.dBam vector by using multiple rounds of PCR, as illustrated in FIG. 4.

(a) First Round PCR

A "mega primer" is generated in a first round of PCR which comprises an AAV 3'-ITR, a tRNA$^{val}$ promoter and ribozyme library genes, using the primers set 1 and 2 listed below:
1) 3'-AAV-ITR primer (44 nt)
   5' A,GGA,<u>AGA,TCT</u>CTG,GCG,CGC,TCG,CTC,GCT, CAC,TGA,GGC,CGC,CCG,G (SEQ ID NO:5) Bgl II site is underlined.
2) 5'-oligo with sequences for tRNA$^{val}$ promoter and ribozyme library genes (tRNA-ribozyme lib PCR, 81 nt)
   5'-TAC,CAG,GTA,ATA,TAC,CAC,AAC,GTG,TGT, TTC,TCT,GGT,NNN,BTT,CTN,NNN,NNN,TGG, ATC,CTG,TTT,CCG,CCC,GGT,TTC,GAA,CCG-3' (SEQ ID NO:6).

The resulting PCR product is purified and used as 5'-megaprimer (AAV-ITR-tRNA-ribozyme library) for a second round PCR to generate the full length AAV vector with ribozyme library gene.

(b) Second Round PCR 1) 3'megaprimer (The product from 1st round PCR)
2) 5'-AAV-ITR
   5' - AGGAA<u>GATCT</u>CAGCAGCTGCGCTCGC T C G C TCACTGAGG-3' (SEQ ID NO:7), Bgl II site is underlined.

Since the resulting DNA is linear, it may require autoligation via the Bgl II Site and/or supercoiling by topoisomerase. The resultant linear form of AAV pro-vector ribozyme gene DNA are purified, and used to generate AAV vector.

In general, the AAV vectors described herein were unexpectedly superior to any previously described because:

A) Proprietary purification methods developed at Immusol yield high titers (up to 10⁹ infectious particles/ml) with no Ad$^{wt}$ contamination. This is in contrast to published data, which state relatively low titers (Hermonat and Muzyczka (1984) *PNAS USA* 81:6466; Samulski et al. (1987) *J. Virol.* 61:3096; Kaplitt et al. (1994) *Nature Genetics* 8:148; Miller et al. (1994) *PNAS USA* 91:10183; Samulski et al. (1989) *J. Virol.* 63:3822). This is important for constructing complete ribozyme libraries, for performing efficient, high m.o.i. transductions as well as making feasible any in vivo (animal) applications of the library or selected libraries.

B) The recombinant AAV of the present invention can integrate (see above) while the literature states that rAAV does not integrate (Flotte et al. (1994) *Am. J. Resp. Cell. Mol. Biol.* 11:517).

C) Once a cell or cells have been selected and shown to contain the ribozyme(s) of interest, the entire AAV-ribozyme expression cassette can be easily "rescued" from the host cell genome by introduction of the AAV viral proteins and wild type adenovirus. This makes isolation, purification and identification of selected ribozymes considerably easier than other molecular biology techniques, all without replication-competent virus.

c. Analysis of the Hairpin Ribozyme Gene Library
  i. Complexity of the Library

The complexity and function of the hairpin ribozyme gene library was analyzed by in vitro cleavage of known target substrates, which included two HIV targets and one HCV target (FIG. 2).

The HIV targets and the HCV target were pol3308 and env7931 and HCV core506, respectively (Townsend and Townsend case No. 016556-000800, Immusol, Inc., Novel Anti-HIV Ribozymes, Leavitt et al.; Welch et al. (1996) *Gene Therapy* 3:994). These were transcribed at 37° C. for 2 hr by using MEGA script High yield Transcription kit (Ambion Inc., Austin, Tex.):

|  | for each DNA sample | control |
|---|---|---|
| H₂O RNAse free | 3.4 μl | 5.4 μl |
| 5x Transcription Buffer | 4 μl | 4 μl |
| DTT 100 mM | 2 μl | 2 μl |
| RNasin (RNAse inhibitor) | 0.6 ul (20 U) | 0.6 ul |
| GTP 2.5 mM | 1 μl | 1 μl |
| ATP 2.5 mM | 1 μl | 1 μl |
| UTP 2.5 mM | 1 μl | 1 μl |
| CTP 2.5 mM | 1 μl | 1 μl |
| CTP P³² labeled (20 Ci) | 2 μl | 2 μl |
| Template DNA linearized | 1 μg | 1 μg |
| T7/SP6 Polymerase (at 15–20 U/μl) | 2 μl | 2 μl |
| Final Volume | 20 μl | 20 μl |

The DNA template was removed by incubating with 1 1 RQ1 RNAse free DNase (Promega) at 37° C. for 15–30 min. Samples were denatured at 65–70° C. for 5 minutes prior to loading onto a (5% polyacrylamide/7 M urea gel for purification. The transcripts of target were excised form the gel by UV shadowing technique, and further extracted by BIO 101 RNaid kit (BIO 101, San Diego Calif.).

The ribozyme library was transcribed in vitro and gel purified as described above, in the absence of [³²P]CTP. Ribozyme/substrate in vitro cleavage was carried out by incubating equimolar amounts of ribozyme library transcript with substrate RNA at 37° C. for 1–3 hour in 40 mM Tris, pH 7.5, 12 mM MgCl₂/2 mM spermidine/0.2 mM EDTA. Reactions were terminated by the addition of 1 vol. of 2×loading buffer (80% formamide, 0.1% bromophenol blue, 0.1% xylene cyanol, 2 mM EDTA). Products of the cleavage reactions are resolved by electrophoresis on 15% acrylamide/7M urea gels and analyzed by autoradiography.

As shown in FIG. 2, the ribozyme library contains a high degree of sequence complexity as determined by its ability to cleave three different RNA substrates known to be cleavable by corresponding ribozyme.

ii. Transfection Optimization of Candidate Cell Lines for rAAV Production

Transfection efficiencies were tested on several candidate cell lines, including Hela, 293, A549, CF2, MDCK, and CHO with five commercially available lipid preparations compared to CaPO₄ using an NGFR reporter plasmid. Two lipids, LipofectAmine (GIBCO/BRL) and DOSPER (Boehringer Mannheim), showed the highest transfection efficiencies on HeLa, 293, A549 and Cf2, using AAV/NGFR and Ad8 in our experimental system followed by FACS analysis as shown in Table 2.

Based on these and other experiments which included A549, we decided to continue with A549, HeLa, and Cf2 cells for further studies. Small scale transfections were set up with LipofectAmine and DOSPER on A549, Hela, and Cf2 cells. Six different volumes of LipofectAmine and Dosper were tested, 0, 3, 6, 10, and 20 ul/ml as well as 3 levels of AAV NGFR and Ad8 DNA, 0.5, 1.5 and 3 µg/ml. The combination of 10 ug/ml LipofectAmine with 1.5 µg/ml of each DNA gave the highest transfection efficiencies.

iii High Titer rAAV Production

AAV particle generation by transient transfection is optimized to yield the highest possible AAV titer with a minimum amount of DNA. This step is crucial for assuring a vector gene library with maximal sequence complexity. Once all the procedures have been optimized, ribozyme gene vector libraries are generated by transient transfection on AAV packaging cell lines and purified by column chromatography. Column purification is carried out only if necessary for optimal transduction efficiency and depending on the desired application. Vector is then applied to a given cell and the desired phenotype is analyzed. Ribozyme sequences in the transduced cells are identified, amplified and rescued with wild type AAV or helper plasmids and helper virus (such as adenovirus). The rescued vector is then used again to transduce the target cells and the cycle repeated. AAV and adenovirus can be selectively inactivated or purified. Any remaining wild type AAV will be inert since it cannot replicate without a helper virus.

Until now, use of AAV as a useful gene delivery vehicle has been hampered by the inability to produce high titer virus (Hermonat and Muzyczka (1984) *PNAS USA* 81:6466; Samulski et al . (1987) *J. Virol.* 61:3096). Indeed, the typical yield of rAAV vectors currently reported in the literature is approximately 105 colony-forming units/ml (Kaplitt et al. (1994) *Nature Genetics* 8:148; Miller et al (1994) *PNAS USA* 91:10183; Samulski et al. (1989) *J. Virol.* 63:3822).

Now, however, proprietary production and purification methods developed at Immusol yield high titers (greater than $5 \times 10^8$ infectious particles/ml) with no wild type helper virus contamination. This is in stark contrast to published data (see references above). High viral titers are extremely important for constructing complete ribozyme libraries; for performing efficient, high m.o.i. transductions as well as making feasible any in vivo (animal) applications of the library or selected libraries.

Immusol, Inc. has previously developed the technology of "increased titer of recombinant AAV vectors by gene transfer with adenovirus coupled to DNA polylysine complexes". This method was published in GENE THERAPY (vol.2, pp429, 1995). This technology is licensed to Immusol and has been used as our routine rAAV preparations for all pre-clinical studies. Recently this technique has been adapted to large-scale preparation of purified rAAV at high titer using $CsCl_2$ centrifugation (Table 3)

Lysing the producer cells with the non-ionic detergent octylglucoside or the ionic detergent deoxycholate appears to increase the titer substantially compared with the freeze-thaw procedure used previously to extract the AAV particles from the cells. Octylglucoside may be of further advantage since it will allow for direct loading of material onto ion-exchange columns if desired (FPLC).

After carefully testing the rAAV titer in the CFU system, we concluded that we can reproducibly obtain high titer purified rAAV. Peak titers are in excess of $5 \times 10^8$/ml (neo colony forming units, CFU). The total yield from a single prep is more than $5 \times 10^9$ CFU at an average titer of $1 \times 10^8$ CFU/ml (Table 3 and data not shown).

iii. Concentration and Purification of rAAV-βgal from Cell Lysate

Recombinant AAV vectors (rAAV) are generally obtained by harvesting and lysing vector producing cells. It has been reported by several groups, however, that much of the rAAV is released into the culture supernatant prior to cell harvesting, generating a loss in vector recovery. Estimates of the amount of rAAV present in the culture supernatant vary from 30–70%. This variability is most likely dependent on when cells are harvested following adenoviral infection. If the amount of rAAV present in culture. supernatant is indeed significant (>50%), then it would be useful, from a production viewpoint, to recover this vector and minimize losses.

In order to produce clinical grade vector it will be necessary to purify the rAAV away from adenovirus as well as removing contaminating nucleic acids. Cellulofine sulfate column chromatography has been used for concentration of rAAV (Tamayose at al., 1996, Human Gene Therapy 7:507–513). However, a small amount of adenovirus as well as various serum and cellular proteins were always co-eluted with rAAV particles from the column. Anion exchange chromatography has been used to purify adenoviral vectors (Huyghe et al., 1996) and anionic resins are known to bind nucleic acids. Previous data indicates that rAAV will not bind to particular anion exchange resins (DEAE and HQ) under physiological salt conditions. Therefore, we developed a chromatography procedure to purify and concentrate rAAV from cell lysate by employing an anion exchange column (HQ) to "pre-clear" a lysate of adenovirus and nucleic acids followed by purifying rAAV with a cation exchange (SP) column.

A summary of the purification data is detailed in Table 8. The results indicate that in addition to removing 99% of the contaminating proteins, the tandem column purification scheme removes adenovirus as well. Therefore, by combining an SP cation exchange column with a tandem HQ anion exchange column we are able to produce highly-purified, adenovirus-free rAAV.

iv. Stability of rAAV Vectors

Various parameters affecting the stability of rAAV vectors were evaluated including storage buffers, storage temperatures, multiple freeze/thaw cycles, benzonase and RQ1 DNase. In summary, we have optimized each parameter resulting in highly stable rAAV vectors showing no significant loss of titers.

(a) Multiple Freeze/Thaws rAAV-NGFR cell lysate was used that had already been frozen/thawed 6 times. Centrifuged (C) and uncentrifuged (U) lysate were frozen and thawed once (C1 and U1), twice (C2 and U2), and three times (C3 and U3) by setting them into the −80 C. for 1.5 hours and then quick thawing(by swirling) in a 37 C. water bath. HeLa cells were transduced with 20 µl and 80 µl of each sample and rAAV-NGFR activity was analyzed by FACS on Day 2. It appears that the rAAV vector can withstand up to 10 freeze/thaw steps stored as either centrifuged or uncentrifuged cell lysate (Table 4).

(b) Glycerol Storage Buffers

The effects of 10% glycerol and 2%FBS/1%Glycerol on −80 C. storage of HPLC purified rAAV-NGFR were studied. Purified rAAV was resuspended in the appropriate buffer and stored at conditions indicated. The next day the whole viral suspension was transduced onto HeLa cells (1e5 cells/well) and analyzed by FACS 48 hours later. Data from Table s indicates that rAAV is stable in both buffers (and maybe slightly more stable in the 10% Glycerol). rAAV also appears to be stable overnight at −80 C. in the buffer in which the vector is eluted off the HPLC.

(c) +4° C. Cell Lysate Stability Studies

The stability of the rAAV when stored at 4 degrees C. in unclarified lysate was studied. It appears that the vector is stable when stored at 4 degrees C. for at least 4 weeks (Table 6). A similar study will be done with HPLC-purified rAAV vector.

(d) Effect of Benzonase/RQ1 DNase Treatment on rAAV Vector Stability

Since Benzonase and RQ1 DNase are adopted in our rAAV production scheme to degrade nucleic acid contaminants, effect of Benzonase or RQ1 DNase on rAAV vector stability and infectivity was evaluated. rAAV-NGFR vector was treated with either Benzonase or DNase. To 100 $\mu$l of the vector was added: 1 $\mu$l 1 M MgCl2 and 1 $\mu$l Benzonase( 280 U/$\mu$l). To another 100 $\mu$l of the vector was added: 1 $\mu$l 1 M MgCl2 and 1 $\mu$l RQ1 DNase (1U/$\mu$l). These tubes were incubated at room temperature for 1 hour. Activity of Benzonase and RQ1 DNase at clearing the RNA in the lysate as well as most of the DNA were verified by gel electrophoresis. The samples were then diluted 1:10 and 10 and 100 $\mu$l of these dilutions were transduced onto HeLa's cells ($10^5$ cells/well) and FACS on Day 2. The results (Table 7) show that neither Benzonase nor RQ1 DNase drastically affects rAAV-NGFR titer. Similar results were obtained when repeated with another vector, rAAV-Neo (data not shown).

Using splinkerette PCR followed by southern blot analysis of the PCR products with radiolabelled AAV-specific probe, we have demonstrated integration of rAAV vector into the target cell chromosome with relatively high efficiency in two cell lines Molt 4/8 and CD 34+ primary human stem cells (FIG. 9 and data not shown). Rather than revealing completely random integration, our data indicated that there are multiple "preferred" sites (hot spots) of rAAV integration (FIG. 9 and data not shown).

d. In vivo Selection of Optimal Ribozyme(s) Against a Defined Target

Target cells are generated that express the target RNA of interest. If the product of the target gene itself is FACS-sortable (i.e. any cell surface protein that is detectable by a specific antibody) or is selectable by various culturing methods (i.e. drug resistance, viral susceptibility, etc.), then one can proceed directly to application of the vector library below. If not, then the target gene sequence is cloned in cis to two separate reporter genes that are either FACS-sortable and/or selectable, for example the green fluorescent protein (GFP) or the nerve growth factor receptor (NGFR) that are FACS-sortable and HSV thymidine kinase (tk) that renders a cell sensitive to gancyclovir. These two target-reporter constructs are then stably transfected into cells (e.g. HeLa or A549) to create the target cells.

The AAV vectors in which the ribozyme library is embedded contain a neo$^r$ gene as a selection marker and for titering purposes. Target cells are grown to 70–80% confluency and transduced with the AAV-ribozyme library at an m.o.i. >1 (to favor multiple transduction events, and multiple ribozyme genes, per cell). Transduction is accomplished by incubating cells with vector overnight at 37° C., as described above. Transduced cells are selected by culturing the cells for 10–14 days in the presence of G418 (400–500 micrograms/ml culture medium).

To determine which cells are expressing ribozymes directed against the target, the transduced cells are sorted and/or selected for the two cis-linked reporter genes (or for the specific gene product if it itself is sortable/selectable). In the reporter system, two different reporters are necessary to distinguish between ribozymes specific for the target or simply recognizing the reporter itself. Cells in which the expression of both reporter genes is reduced are then believed to express ribozymes specific for the target.

The ribozyme vectors present in these surviving cell clones are rescued from the cell by wild type AAV or by transient transfection with packaging plasmids in the presence of adenovirus (Harmonat and Muzyczka (1984) Proc. Natl. Acad. Sci. USA 81:6466; Tratschin et al. (1985) Mol. Cell. Biol. 5:3251; Samulski et al (1982) Proc. Natl. Acad. Sci. USA 79:2077). The rescued vectors are then re-introduced into the untransduced parental cell line under conditions favoring a single ribozyme pro-vector per cell, and reselected or screened.

Once a cell line containing a single specific ribozyme gene is thus deconvoluted, identified, and cloned, the corresponding ribozyme gene found within the cell line is PCR cloned and sequenced using PCR primers described herein. The resulting sequence is expected to be exactly complementary to the gene sequence the ribozyme is inactivating, except that the target RNA must also contain a GUC sequence.

e. Detection of Unknown Genes Which Regulate Leptin Expression

Identification of genes that regulate leptin gene expression (Zhang et al (1994) Nature 372:425) is important for the following reasons: 1) since leptin is involved in obesity, genes that regulate this gene may be potential therapeutic targets, and 2) it serves as an example of how genes that affect transcription from a given promoter may be cloned.

The sequence of the leptin gene and of the promoter regions of the leptin gene have been described (Miller et al. (1996) Proc. Natl. Acad. Sci. USA 93:5507). The transcriptional promoter elements of the leptin gene are PCR cloned directly from known sequence information. They may also be obtained from sources such as the American Type Tissue Culture Collection. Expression vectors are generated whereby either of two reporter genes, NGFR or GFP, are expressed from the leptin promoter. Stable reporter gene-expressing cell lines are derived as described above and selected for expression of NFGR and GFP by Fluorescence-Activated Cell Sorting (FACS) analysis. Clones are selected which express uniform levels of both markers, as homogeneous populations, to yield good signal-to-noise ratios during FACS analysis to facilitate subsequent identification of underexpressing cells. Such clones are obtained by isolating transduced cells that exhibit a uniform level of fluorescence using by FACS, and then cloning these cells.

Cell clones are transduced with the AAV random ribozyme gene vector library at a high multiplicity of infection (m.o.i. >1) and selected in G418. Cells expressing both reporter genes are then selected by FACS analysis and under-expressing and over-expressing clonal cell lines are generated, since any alteration in reporter gene expression may indicate a target responsible for leptin gene regulation. Since these cell clones are isolated from cells that were transduced at a high multiplicity of infection, many contain multiple ribozyme genes. AAVs that contain ribozyme genes are rescued from the different under-expressing or over-expressing cell clones as described above (Section 2.b.iv.a). These rescued AAVs are used to transduce fresh cells at a low multiplicity of infection. After G418 selection, under-expressing or over-expressing clones are once again obtained by FACS. This time however, each clonal cell line expresses only a single ribozyme gene. The presence of a single ribozyme gene is confirmed by rescue of the AAV genome and sequence analysis of the ribozyme gene(s).

Individual ribozyme genes that cause under-expression or over-expression of reporter genes that are operably linked to the leptin promoter are then transduced into cells that express the leptin gene itself. Individual clonal isolates are screened for expression of the leptin gene by RNase protection and protein immunoblot assays (Sambrook, et al.). Activity of specific ribozymes is verified using the corresponding disabled ribozyme (mutation of loop 2 AAA to UGC, see Section 2.f) Cell clones with altered leptin gene expression are selected for further study.

The sequence of the ribozyme binding arms is combined with the requisite GUC to construct a DNA probe (5'XXXXXXXNGUCXXXX3', where X is the deduced sequence coming from the specific ribozyme), which is then used to screen cDNA libraries (Sambrook et al) to clone the gene or genes whose inactivation modulates leptin expression.

f. Detection of Cell Cycle Regulatory Genes

P21, also known as Cip 1 (CDK-interacting protein) is a negative regulator of mammalian cell cycle progression. Overexpression of human P21 efficiently arrests vascular smooth muscle cells (VSMC) in the $G_1$ phase of the cell cycle and results in a 60% reduction in VSMC proliferation following growth factor simulation in vitro (Chang et al., 1995 *J. Clin. Invest.* 96: 2260–2268). Genes involved in p21 gene expression are identified by a protocol similar to that described for leptin gene regulation, except the p21 promoter elements will be used to drive the expression of the reporter genes, NGFR or GFP. Individual ribozyme genes that cause under-expression of the reporter genes are used to isolate genes that activate the cell cycle, while those ribozymes that cause over-expression of reporter genes can be used to identify genes that transrepress cell cycle.

g. Identification of an Unknown Gene Responsible for Tumor Suppression or Tumorigenesis Identification of an unknown gene responsible for tumor suppression is accomplished by:

transducing 3T3, J82, U-138 MG, A549 or any primary cell line with the AAV-ribozyme library. Optimally, the cells are primary cells with no tumor phenotype or partially transformed or immortalized cells that show little to no tumor growth in nude mice (O'Toole et al. (1978) *Br. J. Cancer* 38:64; Ponten et al . (1971) *Hum Hered.* 21:238).

selecting cells that were transduced by the AAV-ribozyme using G418 selection (AAV carries neomycin resistance gene).

plating all transduced cells in soft agar, to assay anchorage dependence (Renshaw et al. (1995) *Mol. Cell. Biol.* 15:1286; Sawyers et al. (1992) *Cell* 70:901), and in minimal media, to assay growth factor dependence (Renshaw et al. (1995) *Mol. Cell. Biol.* 15:1286; Renshaw et al. (1992) *Embo J.* 11:3941). Both are widely used indicators of cellular transformation in cell culture.

picking and expanding the resulting soft agar and minimal media colonies.

Since growth factor and anchorage independence are not always sufficient to allow tumor formation in an animal, ribozyme-expressing cells are optionally further selected by injection into nude mice. Tumors that form are isolated and the AAV-ribozyme genome is rescued and the assays are repeated. Once specific ribozymes have been selected, their activity is verified to be due to RNA cleavage and not simply antisense as previously described. The selected ribozyme genes are amplified by PCR, cloned and sequenced. The sequence of the ribozyme binding arms is combined with the requisite GUC to construct a DNA probe (5'XXXXXXXNGUCXXXX3', where X is the deduced sequence coming from the specific ribozyme), which is then used to screen cDNA libraries to clone the gene whose inactivation results in tumor formation.

Identification of an unknown gene responsible for tumorigenesis is accomplished by:

transducing isolated primary tumor cells or any transformed cell line with AAV-ribozyme library;

selecting cells that were transduced by the AAV-ribozyme using G418 selection (AAV carries neomycin resistance gene);

plating the selected cells and allowing them to reach confluence;

treat the confluent cultures with bromo-deoxyuridine (BrdU), a nucleoside analog that is toxic to any cell that is actively dividing. All cells that remain non-contact inhibited in the culture will die. Cells that received a ribozyme gene that inactivates the oncogene responsible for the tumorigenesis will not be growing in a confluent culture due to contact inhibition. Untransformed cells are contact inhibited and are arrested in quiescence, transformed cells are not and will continue to grow on top of each other as long as they are fed;

Pick and expand the surviving cells. Rescue the AAV-ribozyme genome and sequence to identify the gene responsible for the tumor. In addition to identifying an oncogene, one also now has in hand a ribozyme capable of inactivating said oncogene, which may be applicable to cancer gene therapy.

This method is also useful to determine the genetic cause for, and possibly deduce a ribozyme therapy against, a particular isolated tumor from a patient—i.e. patient-by-patient specific cancer gene therapy.

h. Detection of an Unknown Gene Responsible for Apoptosis

Programmed cell death or apoptosis is essential for normal development. Deregulation of apoptosis can lead to a spectrum of defects ranging from embryo lethality, to perturbation of post-natal development and even to cancer. Identification of genes that modulate the regulation of apoptosis provides an opportunity for the treatment of numerous diseases including cancer, neuronal degeneration, lymphoproliferation, inflammation and immunodeficiency, among others.

Apoptosis can be triggered in a variety of ways, depending on the cell type (for review see McConkey et al (1996) Molecular Aspects of Medicine 17:1). To identify genes involved in apoptosis, the AAV ribozyme gene vector library is transduced into appropriate cells and selected with G418. The cells are then triggered to undergo apoptosis. Any cells that subsequently survive are grown up and the ribozyme gene or genes responsible are cloned out of the rescued AAV vectors (as described in the previous sections. Genes involved in the apoptotic pathway can then be cloned, again based on the sequence of the ribozyme binding arms and GUC (see above sections).

Apoptosis can be measured by numerous ways. Loss of cell viability (failure to either excluded vital dye or uptake MTT), DNA fragmentation (assayed by) agarose gel electrophoresis, PFG electrophoresis, in situ tunnel (terminal transferase labeling), cell and nuclear morphology (microscopy to visualize chromatin condensation, DNA organization, and cytoplasmic integrity), cysteine protease activation (PARP or lamin cleavage in vivo or in vitro, an inhibition by cysteine protease inhibitors), sub G1 peak by FACS analysis, and inhibition by Bcl-2, are some of the means for measuring apoptosis.

One of the most important effectors of apoptosis is the ICE gene family (Interleukin-1 (Converting Enzyme). Mutations of ced-3/ICE gene prevent apoptotic death in cells and overexpression if ICE gene in a number of cell types induce apoptosis (Thornberry, N. A. et al., 1992. *Nature* 356:768–774; Miura, M. et al., 1993. *Cell* 78:653–660; Gagliardini, V. et al., 1994. *J. Biol. Chem.,* 268:826–828).

Identification of genes that regulate ICE gene expression are accomplished by protocol similar to that listed in Example e except that reporter genes (NGFR or GFP) are expressed from the ICE promoter.

j. Screening for Transactivator or Transsuppressor for HPV URR or HIV.

HPVs are present in many anogenital tumors, including anal, penile, vagina, and vulvar cancers. The transforming effects of the proteins of HPVs are mediated through interactions with cellular proteins. The E6 protein of the "high risk" HPVs binds to the tumor suppressor p53 protein, and hastens its degradation (ref). The E7 protein can cooperate with an activated ras oncogene (ref), binds to a tumor suppressor, the cellular retinoblastoma gene product (pRB) and inhibits its function. The expression of the transforming genes of HPVs is controlled by both viral and cellular factors. The major regulatory region in the genome is the upstream regulatory region (URR).

Sites that have been identified and located in the URR include binding sites of the cellular factors P92, Sp1, Ap1, Oct-1, Ap2, TEF-1, PR, NFA, and PVF. Cellular factors that act at these sites have been studied in cervical epithelium, and probably have equivalents in other epithelia (ref).

Since expression of papillomavirus genes can be affected positively or negatively by so many trans- and cis-acting factors, there is a clear potential to modify expression of viral genes by providing a tumor cell with the appropriate factors.

Identification of unknown transactivator and transsuppressor for HPV URR is accomplished by a protocol similar to that listed in Example except that reporter genes (NGFR or GFP) are expressed from the HPV URR or HIV gene promoter.

The preceding examples are merely illustrative and are not intended to limit the invention in any way. All references mentioned herein are hereby incorporated in their entirety for all purposes. The present invention is related to U.S. application Ser. Nos. 081664,094 and 08/719,953), which are hereby incorporated by reference. Reference is also made to provisional application serial No. 60/027,875.

Sequences

5' Primer (37 nt):

5'GGGT<u>AATACGACTCACTATA</u>GGGATCCTCGA TGAAGC3' (SEQ ID NO1)

3' Synth Primer (76 nt):

5'TCGACGCGTACCAGGTAATATACCA-CAACGTGTGTTTCTCTGGTNNNNTTCT NNNNNNNGCTTCATCGAGGATCCC3' (SEQ ID NO:2)

3' Primer:

5'TCGACGCGTACCAGGTAATATACCACAACGTG TGTTTCTCTGGT3'(SEQ ID NO:3)

3' Disabled Primer:

5'TCGACGCGTACCAGGTAATATACCACAACGTG TGACGCTCTGGT3' (SEQ ID NO:4)

3'-AAV-ITR primer:

5'AGGAAGATCTCTGGCGCGCTCGCTCGCTCACT GAGGCCGCCCGG3' (SEQ ID NO:5)

tRNA-Rz lib primer:

5'TACCAGGTAATATACCACAACGTGTGT TTCTCTGGTNNNBTTCTNNNNNNNTGGATC CTGTTTCCGCCCGGTTTCGAACCG3' (SEQ ID NO:6)

5'-AAV-ITR primer:

5'-AGGAAGATCTCAGCAGCTGCGCGCTCGCTCGC TCACTGAGG-3' (SEQ ID NO:7)

Notes:

T7 promoter sequence: <u>underlined</u>

Ribozyme sequence: bold

BamHI, MluI or Bgl II restriction enzyme sites: *italic*

3 nt disabling mutation: <u><u>double underlined</u></u>

What is claimed is:

1. A method of identifying regulatory gene products and genes that control the expression of a particular selected gene, comprising the steps of:

a. co-expressing in a same cell a selected reporter gene operably linked to a promoter of a selected gene and at least one member of a library of hairpin ribozyme-encoding nucleic acids having randomized recognition sequences, wherein a mRNA encoded by said reporter gene is not recognized or cleaved by a ribozyme expressed in said cell;

b. identifying and cloning a cell wherein the level of expression of the reporter gene is measurably different from that of a cell that expresses the reporter gene but does not express said at least one member of the library of hairpin ribozyme-encoding nucleic acids;

c. identifying a nucleic acid expressed in the cells cloned in step b whose gene product is recognized by a ribozyme expressed in said cloned cells.

2. A method according to claim 1, comprising a. operably linking the promoter of a selected gene to a first reporter gene in a vector b. transducing a population of cells with a vector of step a;

c. identifying and cloning a transduced cell that contains a vector of step a, to yield a population of cloned cells that contain said vector;

d. transducing cloned cells of step c with vectors that comprise a library of hairpin ribozyme-encoding nucleic acids having randomized recognition sequences, wherein the vectors further comprise at least one reporter gene different from the reporter gene of step a;

e. identifying and cloning a transduced cell that contains the vectors of steps a and d wherein the level of expression of the reporter gene is measurably different from the cells of step c, to yield cloned transduced cells that contain the vectors of steps a and d wherein the level of expression of the reporter gene is measurably different from the cells of step c;

f. isolating the nucleic acid that encodes the ribozyme that is expressed in said cloned transduced cells of step e;

g. determining the sequence of the recognition sequence of the ribozyme of step f;

h. making an oligonucleotide consisting of the recognition sequence, including a GUC cleavage site, of the ribozyme of step h;

i. identifying a nucleic acid whose gene product is recognized by the ribozyme of step g using the oligonucleotide of step h as a probe.

3. A method according to claim 1, wherein the selected gene is a leptin gene.

4. A method according to claim 1, wherein the hairpin ribozyme-encoding nucleic acid is operably linked to an inducible promoter.

5. A method according to claim 1, wherein the hairpin ribozyme-encoding nucleic acid is expressed from a viral vector.

6. An in vivo method of selecting at least one hairpin ribozyme that cleaves a target recognition site in a target nucleic acid, comprising the steps of:

a. transducing a population of cells with a vector expressing a library of hairpin ribozyme-encoding nucleic acids having randomized recognition sequences, and with a nucleic acid that encodes at least one FACS-sortable reporter gene, under conditions that result in the expression of multiple different ribozymes per cell;

b. selecting and cloning transduced cells that express at least one ribozyme-encoding nucleic acid whose gene product cleaves a target sequence in a selected target nucleic acid;

c. isolating the ribozyme-encoding nucleic acids from the cloned cells of step b;

d. packaging the ribozyme-encoding nucleic acids of step c;

e. transducing a population of cells with the packaged ribozyme-encoding nucleic acids of step d;

f. selecting and cloning transduced cells of step e that express at least one ribozyme-encoding nucleic acid whose gene product cleaves a target sequence; and g. isolating the ribozyme-encoding nucleic acid from the cloned cells of step f.

* * * * *